(12) United States Patent
Schoenafinger et al.

(10) Patent No.: US 8,344,004 B2
(45) Date of Patent: Jan. 1, 2013

(54) CYCLIC PYRIDYL-N-[1,3,4]-THIADIAZOL-2-YL-BENZENE SULFONAMIDES, PROCESSES FOR THEIR PREPARATION AND THEIR USE AS PHARMACEUTICALS

(75) Inventors: Karl Schoenafinger, Alzenau (DE); Stefanie Keil, Frankfurt am Main (DE); Matthias Urmann, Frankfurt am Main (DE); Hans Matter, Frankfurt am Main (DE); Maike Glien, Frankfurt am Main (DE); Wolfgang Wendler, Frankfurt am Main (DE); Ulrike Wendler, legal representative, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/796,886

(22) Filed: Jun. 9, 2010

(65) Prior Publication Data

US 2011/0224263 A1    Sep. 15, 2011

Related U.S. Application Data

(63) Continuation of application No. PCT/EP2008/010559, filed on Dec. 12, 2008.

(30) Foreign Application Priority Data

Dec. 26, 2007   (EP) ..................... 07291626

(51) Int. Cl.
*A61K 31/4439* (2006.01)
*A61K 31/433* (2006.01)
*C07D 417/12* (2006.01)

(52) U.S. Cl. ..................... 514/342; 514/279; 546/268.7; 548/130

(58) Field of Classification Search .................. 514/342, 514/279; 546/268.7; 548/130
See application file for complete search history.

(56) References Cited

U.S. PATENT DOCUMENTS 4,837,303 A * 6/1989 Jung .............................. 530/311

FOREIGN PATENT DOCUMENTS

| WO | WO 97/40017 | 10/1997 |
|---|---|---|
| WO | WO 2005/005421 | 1/2005 |
| WO | WO 2007/039171 | 4/2007 |
| WO | WO 2007/039173 | 4/2007 |

OTHER PUBLICATIONS

Khimiko-Farmatsevticheskil Zhurnal, vol. 21, No. 8, pp. 965-968, (1987).

* cited by examiner

*Primary Examiner* — Sreeni Padmanabhan
*Assistant Examiner* — Sahar Javanmard
(74) *Attorney, Agent, or Firm* — Scully, Scott, Murphy & Presser, P.C.

(57) ABSTRACT

The invention relates to cyclic N-[1,3,4]-thiadiazol-2-yl-benzene sulfonamides and to their physiologically acceptable salts and physiologically functional derivatives showing PPARdelta or PPARdelta and PPARgamma agonist activity. What is described are compounds of the formula I,

I

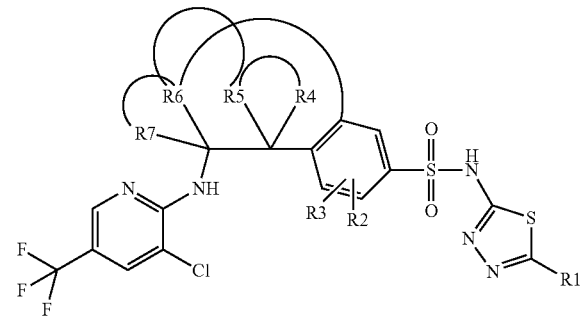

in which the radicals are as defined, and their physiologically acceptable salts and processes for their preparations. The compounds are suitable for the treatment and/or prevention of disorders of fatty acid metabolism and glucose utilization disorders as well as of disorders in which insulin resistance is involved and demyelinating and other neurodegenerative disorders of the central and peripheral nervous system.

14 Claims, No Drawings

CYCLIC PYRIDYL-N-[1,3,4]-THIADIAZOL-2-YL-BENZENE SULFONAMIDES, PROCESSES FOR THEIR PREPARATION AND THEIR USE AS PHARMACEUTICALS

This application is a Continuation of International Application No. PCT/EP2008/010559, filed Dec. 12, 2008, which is incorporated herein by reference in its entirety.

The invention relates to cyclic N-[1,3,4]-thiadiazol-2-yl-benzene sulfonamides and to their physiologically acceptable salts and physiologically functional derivatives showing PPARdelta or PPARdelta and PPARgamma agonist activity.

Benzenesulfonamino compounds which bind to PPARs are described in WO 2005/005421 and WO 2007/039173. Sulfonamide compounds showing hypoglycemic activity are disclosed in Khimiko-Farmatsevticheskii Zhurnal (1987), 21(8), 965-8. From WO 97/40017 compounds having a phenyl group linked to heterocycles are known as modulators of molecules with phosphotyrosine recognition units.

The invention is based on the object of providing compounds which permit therapeutically utilizable modulation of lipid and/or carbohydrate metabolism and are thus suitable for the prevention and/or treatment of diseases such as type 2 diabetes and atherosclerosis and the diverse sequelae thereof. Another purpose of the invention is to treat demyelinating and other neurodegenerative disorders of the central and peripheral nervous systems.

A series of compounds which modulate the activity of PPA receptors has been found. The compounds are suitable in particular for activating PPARdelta or PPARdelta and PPARgamma, however it is possible that the relative activation varies depending on the specific compounds.

Compounds of the present invention are described by formula I:

formula I

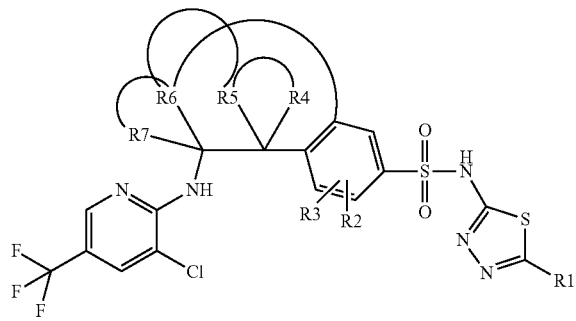

wherein

R1 is (C1-C6)alkyl, (C0-C6)alkylene(C3-C6)cycloalkyl, (C0-C6)alkylene-O—(C1-C6)alkyl, (C0-C6)alkylene-O—(C3-C6)cycloalkyl, (C0-C6)alkylene-(C6-C14)aryl, (C0-C6)alkylene-(C5-C15)heteroaryl, wherein alkyl, alkylene, aryl, heteroaryl and cycloalkyl can be unsubstituted or mono-, di- or trisubstituted by F, Cl, Br, (C1-C6)alkyl, O—(C1-C6)alkyl, $CF_3$, $OCF_3$, CN, CO—(C1-C6)alkyl, COO(C1-C6)alkyl, CON((C0-C6)alkylene-H)((C0-C6)alkylene-H), $S(O)_m$(C1-C6)alkyl;

R2, R3 are independently H, halogen, (C1-C6)alkyl, (C0-C4)alkylene-O—(C0-C4)alkylene-H, CN, COO(C1-C6)alkyl, CON((C0-C6)alkylene-H)((C0-C6)alkylene-H), $S(O)_m$(C1-C6)alkyl, wherein alkyl and alkylene are unsubstituted or mono-, di- or trisubstituted by F;

R4, R5, R6 and R7 are independently H, (C1-C6)alkyl, (C0-C6)alkylene-(C3-C6)cycloalkyl, (C0-C6)alkylene-(C6-C14)aryl, (C0-C6)alkylene-(C5-C15)heteroaryl, (C0-C6)alkylene-(C3-C15)heterocycloalkyl, (C0-C6)alkylene-(C3-C15)heterocycloalkenyl, wherein alkyl, alkylene and cycloalkyl are unsubstituted or mono-, di- or trisubstituted by halogen, (C1-C6)alkyl, (C0-C6)alkylene-O—(C0-C6)-alkylene-H, $CF_3$, $OCF_3$, CN, CO—(C1-C6)alkyl, COO—(C1-C6)alkyl, CON((C0-C6)alkylene-H)((C0-C6)alkylene-H), $S(O)_m$(C1-C6)alkyl, and wherein aryl, cycloalkyl, heterocycloalkyl, heterocycloalkenyl and heteroaryl are unsubstituted or mono-, di- or trisubstituted by halogen, CF3, (C1-C6)alkyl and (C0-C4)alkylene-O—(C0-C4)alkylene-H, and wherein at least one pair of R4 and R5, R6 and R7, R5 and R6, together with the C-atoms to which they are connected, or R6 together with the ortho C-atom of the aromatic ring, form a (C3-C9)cycloalkyl, a (C3-C9)-heterocycloalkyl or a (C3-C9)-heterocycloalkenyl, wherein cycloalkyl, heterocycloalkyl and heterocycloalkenyl are unsubstituted or mono-, di- or trisubstituted by halogen, CF3, (C1-C6)alkyl and (C0-C4)alkylene-O—(C0-C4)alkylene-H;

m is 0, 1, 2;

in all its stereoisomeric forms, enantiomeric forms and mixtures in any ratio, and its physiologically acceptable salts and tautomeric forms.

Another embodiment according to the invention are compounds of the formula I, wherein R1 is (C1-C6)alkyl, (C0-C6)alkylene(C3-C6)cycloalkyl, (C0-C6)alkylene-(C6-C14)aryl, (C0-C6)alkylene-(C5-C15)heteroaryl, wherein alkyl, alkylene, aryl, heteroaryl and cycloalkyl can be unsubstituted or mono-, di- or trisubstituted by F, Cl, Br, (C1-C6)alkyl, O—(C1-C6)alkyl, $CF_3$, $OCF_3$, CN;

R2, R3 are independently H, halogen, (C1-C6)alkyl, (C0-C4)alkylene-O—(C0-C4)alkylene-H, CN, COO(C1-C6)alkyl, wherein alkyl and alkylene are unsubstituted or mono-, di- or trisubstituted by F;

R4, R5, R6 and R7 are independently H, (C1-C6)alkyl, (C0-C6)alkylene-(C3-C6)cycloalkyl, (C0-C6)alkylene-(C6-C14)aryl, wherein alkyl, alkylene and cycloalkyl are unsubstituted or mono-, di- or trisubstituted by halogen, (C1-C6)alkyl, (C0-C6)alkylene-O—(C0-C6)-alkylene-H, $CF_3$, and wherein alkyl and cycloalkyl are unsubstituted or mono-, di- or trisubstituted by halogen, CF3, (C1-C6)alkyl and (C0-C4)alkylene-O—(C0-C4)alkylene-H, and wherein at least one pair of R4 and R5, R6 and R7, R5 and R6, together with the C-atoms to which they are connected, or R6 together with the ortho C-Atom of the aromatic ring, form a (C3-C9)cycloalkyl, a (C3-C9)-heterocycloalkyl wherein cycloalkyl and heterocycloalkyl are unsubstituted or mono-, di- or trisubstituted by halogen, CF3, (C1-C6)alkyl and (C0-C4)alkylene-O—(C0-C4)alkylene-H;

in all its stereoisomeric forms, enantiomeric forms and mixtures in any ratio, and its physiologically acceptable salts and tautomeric forms.

Another embodiment according to the invention are compounds of the formula I, wherein R1 is (C1-C6)alkyl, (C0-C6)alkylene-(C3-C6)cycloalkyl, (C0-C6)alkylene-(C6-C14)aryl, wherein alkyl, alkylene, aryl, and cycloalkyl can be unsubstituted or mono-, di- or trisubstituted by F;

in all its stereoisomeric forms, enantiomeric forms and mixtures in any ratio, and its physiologically acceptable salts and tautomeric forms.

Another embodiment according to the invention are compounds of the formula I, wherein R1 is (C1-C6)alkyl, (C3-C6)cycloalkyl or (C6-C14)aryl, wherein alkyl can be unsubstituted or mono-, di- or trisubstituted by F;

in all its stereoisomeric forms, enantiomeric forms and mixtures in any ratio, and its physiologically acceptable salts and tautomeric forms.

Another embodiment according to the invention are compounds of the formula I, wherein R2 and R3 are independently H, halogen, (C1-C6)alkyl, (C0-C4)alkylene-O—(C0-C4)alkylene-H, wherein alkyl and alkylene are unsubstituted or mono-, di- or trisubstituted by F;

in all its stereoisomeric forms, enantiomeric forms and mixtures in any ratio, and its physiologically acceptable salts and tautomeric forms.

Another embodiment according to the invention are compounds of the formula I, wherein R2 is H, halogen, (C1-C6)alkyl, O—(C0-C4)alkylene-H, wherein alkyl and alkylene are unsubstituted or mono-, di- or trisubstituted by F; and R3 is H;

in all its stereoisomeric forms, enantiomeric forms and mixtures in any ratio, and its physiologically acceptable salts and tautomeric forms.

Another embodiment according to the invention are compounds of the formula I, wherein R4, R5, R6 and R7 are independently H or (C1-C6), and wherein at least one pair of R4 and R5 or R5 and R6 together with the C-atoms to which they are connected, or R6 together with the ortho C-atom of the aromatic ring, form a (C3-C9)cycloalkyl, wherein cycloalkyl is unsubstituted or monosubstituted by (C1-C6)alkyl;

in all its stereoisomeric forms, enantiomeric forms and mixtures in any ratio, and its physiologically acceptable salts and tautomeric forms.

Another embodiment according to the invention are compounds of the formula I, wherein R1 is (C1-C6)alkyl, (C3-C6)cycloalkyl or phenyl, wherein alkyl is unsubstituted or mono-, di- or trisubstituted by F, R2, R3 are independently H, halogen, (C1-C6)alkyl, O—(C1-C4)alkylene-H, wherein alkyl and alkylene are unsubstituted or mono-, di- or trisubstituted by F;

R4, R5, R6 and R7 are independently H, (C1-C6)alkyl, wherein alkyl is unsubstituted or mono-, di- or trisubstituted by halogen or (C1-C6)alkyl and wherein at least one pair of R4 and R5, R6 and R7, R5 and R6, together with the C-atoms to which they are connected, or R6 together with the ortho C-atom of the aromatic ring, form a (C3-C7)cycloalkyl, wherein cycloalkyl is unsubstituted or mono-, di- or trisubstituted by (C1-C6)alkyl;

in all its stereoisomeric forms, enantiomeric forms and mixtures in any ratio, and its physiologically acceptable salts and tautomeric forms.

Another embodiment according to the invention are compounds of the formula I, wherein R1 is (C1-C6)alkyl, which is unsubstituted or mono-, di- or trisubstituted by F;

R2, R3 are H;

R4 and R7 are H;

the pair of R5 and R6 together with the C-atoms to which they are connected form a (C3-C7)cycloalkyl;

in all its stereoisomeric forms, enantiomeric forms and mixtures in any ratio, and its physiologically acceptable salts and tautomeric forms.

Another embodiment according to the invention are compounds of the formula I, wherein R1 is (C1-C6)alkyl, which is unsubstituted or mono-, di- or trisubstituted by F;

R2, R3 are H;

R6 and R7 are H;

the pair of R4 and R5 together with the C-atomes to which they are connected form a (C3-C7)cycloalkyl;

in all its stereoisomeric forms, enantiomeric forms and mixtures in any ratio, and its physiologically acceptable salts and tautomeric forms.

Another embodiment according to the invention are compounds of the formula I, wherein R1 is (C1-C6)alkyl, (C3-C6)cycloalkyl or phenyl, wherein alkyl is unsubstituted or mono-, di- or trisubstituted by F;

R2 is H, Cl, (C1-C4)alkyl, O—(C1-C4)alkylene-H, wherein alkyl and alkylene are unsubstituted or mono-, di- or trisubstituted by F;

R3, R5, R7 are H;

R4 is H or (C1-C4)alkyl;

R6 together with the ortho C-atom of the aromatic ring form a (C3-C7)cycloalkyl, wherein cycloalkyl is unsubstituted or substituted by (C1-C4)alkyl;

in all its stereoisomeric forms, enantiomeric forms and mixtures in any ratio, and its physiologically acceptable salts and tautomeric forms.

Another embodiment according to the invention are the compounds:

4-{1-[(3-Chloro-5-trifluoromethyl-pyridin-2-ylamino)-methyl]-cyclohexyl}-N-(5-isopropyl-[1,3,4]thiadiazol-2-yl)-benzenesulfonamide Trans-4-[2-(3-Chloro-5-trifluoromethyl-pyridin-2-ylamino)-cyclopentyl]-N-(5-isopropyl-[1,3,4]thiadiazol-2-yl)-benzenesulfonamide Cis-4-[2-(3-Chloro-5-trifluoromethyl-pyridin-2-ylamino)-cyclopentyl]-N-(5-isopropyl-[1,3,4]thiadiazol-2-yl)-benzenesulfonamide 4-[2-(3-Chloro-5-trifluoromethyl-pyridin-2-ylamino)-cyclopentyl]-N-(5-isopropyl-[1,3,4]thiadiazol-2-yl)benzenesulfonamide 2-(3-Chloro-5-trifluoromethyl-pyridin-2-ylamino)-indan-5-sulfonic acid (5-isopropyl-[1,3,4]thiadiazol-2-yl)-amide 4-{1-[(3-Chloro-5-trifluoromethyl-pyridin-2-ylamino)-methyl]-cyclopentyl}-N-(5-trifluoromethyl-[1,3,4]thiadiazol-2-yl)-benzenesulfonamide Trans-4-[2-(3-Chloro-5-trifluoromethyl-pyridin-2-ylamino)-cyclopentyl]-N-(5-trifluoromethyl-[1,3,4]thiadiazol-2-yl)benzenesulfonamide 6-Chloro-2-(3-chloro-5-trifluoromethyl-pyridin-2-ylamino)-indan-5-sulfonic acid (5-isopropyl-[1,3,4]thiadiazol-2-yl)-amide 2-(3-Chloro-5-trifluoromethyl-pyridin-2-ylamino)-indan-5-sulfonic acid (5-trifluoromethyl-[1,3,4]thiadiazol-2-yl)-amide 2-(3-Chloro-5-trifluoromethyl-pyridin-2-ylamino)-6-methoxy-indan-5-sulfonic acid (5-isopropyl-[1,3,4]thiadiazol-2-yl)-amide 2-(3-Chloro-5-trifluoromethyl-pyridin-2-ylamino)-indan-5-sulfonic acid (5-phenyl-[1,3,4]thiadiazol-2-yl)-amide 2-(3-Chloro-5-trifluoromethyl-pyridin-2-ylamino)-indan-5-sulfonic acid (5-cyclohexyl-[1,3,4]thiadiazol-2-yl)-amide 2-(3-Chloro-5-trifluoromethyl-pyridin-2-ylamino)-indan-5-sulfonic acid (5-cyclopropyl-[1,3,4]thiadiazol-2-yl)-amide 2-(3-Chloro-5-trifluoromethyl-pyridin-2-ylamino)-3-methyl-indan-5-sulfonic acid (5-isopropyl-[1,3,4]thiadiazol-2-yl)-amide 2-(3-Chloro-5-trifluoromethyl-pyridin-2-ylamino)-6-methyl-indan-5-sulfonic acid (5-isopropyl-[1,3,4]thiadiazol-2-yl)amide 4-{1-[(3-Chloro-5-trifluoromethyl-pyridin-2-ylamino)-methyl]-cyclobutyl}-N-(5-isopropyl-[1,3,4]thiadiazol-2-yl)-benzenesulfonamide 2-(3-Chloro-5-trifluoromethyl-pyridin-2-ylamino)-6-(2,2,2-trifluoro-ethoxy)-indan-5-sulfonic acid (5-isopropyl-[1,3,4]thiadiazol-2-yl)amide This invention also encompasses all combinations of preferred aspects of the invention described herein.

As used herein, the term alkyl is to be understood in the broadest sense to mean saturated hydrocarbon residues which can be linear, i.e. straight-chain, or branched. If not otherwise defined alkyl has 1 to 8 carbon atoms. Examples of "—(C1-C8)-alkyl" are alkyl residues containing 1, 2, 3, 4, 5, 6, 7 or 8 carbon atoms are methyl, ethyl, propyl, butyl, pentyl, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. The term "—(C0-C6)-alkyl" is a hydrocarbon residue containing 1, 2, 3, 4, 5 or 6 carbon atoms, in which the term "—C0-alkyl" is a covalent bond. All these statements apply also to the term alkylene.

As used herein, the term alkenyl is to be understood in the broadest sense to mean hydrocarbon residues which has 1 to 4 double bonds and can be linear, i.e. straight-chain, or branched. If not otherwise defined alkenyl has 2 to 8 carbon atoms. Examples of "—(C2-C8)-alkenyl" are alkenyl residues containing 2, 3, 4, 5, 6, 7 or 8 carbon atoms are, for example vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl. All these statements apply also to the term alkenylene.

As used herein, the term alkinyl is to be understood in the broadest sense to mean hydrocarbon residues, which has 1 to 4 triple bonds and can be linear, i.e. straight-chain, or branched. If not otherwise defined alkinyl has 2 to 8 carbon atoms. Examples of "—(C2-C8)-alkinyl" are alkinyl residues containing 2, 3, 4, 5, 6, 7 or 8 carbon atoms are, for example ethynyl, 1-propynyl, 2-propynyl (=propargyl) or 2-butynyl. All these statements apply also to the term alkylidene.

All these statements also apply if an alkyl group occurs as a substituent on another residue, for example in an alkyloxy residue, an alkyloxycarbonyl residue or an arylalkyl residue.

If not otherwise defined, alkyl, alkylene, alkenyl, alkenylene, alkinyl and alkinylene are unsubstituted or mono-, di- or trisubstituted independently of one another by suitable groups such as, for example: F, Cl, Br, I, CF3, NO2, CN, COON, CO—O—(C0-C4) alkylene-(C6-C10)aryl, CO—O—(C1-C4)alkyl, CO—O—(C0-C4)alkylene-(C3-C13)cycloalkyl, CO—O—(C0-C4)alkylene-(C3-C15)heterocycle, CO—N((C0-C4) alkylene-H)—(C0-C4)alkylene-(C6-C10)aryl, CO—N((C0-C4)alkylene-H)—(C0-C4)alkylene-H, CO—N((C0-C4)alkylene-H)—(C0-C4)alkylene-(C3-C13)cycloalkyl, CO—N((C0-C4)alkylene-H)—(C0-C4)alkylene-(C3-C15)heterocycle, (C0-C4)alkylene-(C3-C6)cycloalkyl, (C0-C4)alkylene-(C6-C10)aryl, (C0-C4)alkylene-(C3-C15)heterocycle, (C2-C6)-alkenyl, (C2-C6)-alkinyl, O—(C0-C6)-alkyl, O—(C0-C4)alkylene-(C6-C10)aryl, O—(C0-C4)alkylene-(C3-C12)cycloalkyl, O—(C0-C4)alkylene-(C3-C15)heterocycle, O—CO—O—(C0-C4)alkylene-(C6-C10)aryl, O—CO—O—(C1-C4)alkyl, O—CO—O—(C0-C4) alkylene-(C3-C13)cycloalkyl, O—CO—O—(C0-C4)alkylene-(C3-C15)heterocycle, S—(C1-C4)alkyl, S—(C0-C4)alkylene-(C3-C13)cycloalkyl, S—(C0-C4)alkylene-(C6-C10)aryl, S—(C0-C4)alkylene-(C3-C15)heterocycle, SO—(C1-C4)alkyl, SO—(C0-C4)alkylene-(C3-C13)cycloalkyl, SO—(C0-C4)alkylene-(C6-C10)aryl, SO—(C0-C4)alkylene-(C3-C15)heterocycle, SO2-(C1-C4)alkyl, SO2-(C0-C4)alkylene-(C3-C13)cycloalkyl, SO2-(C0-C4)alkylene-(C6-C10)aryl, SO2-(C0-C4)alkylene-(C3-C15)heterocycle, SO2-N((C0-C4)alkylene-H)—(C0-C4)alkylene-(C6-C10)aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15)heterocycle where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4) alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4)alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl ring or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term cycloalkyl is to be understood to mean saturated hydrocarbon cycle containing from 3 to 13 carbon atoms in a mono- or bicyclic, fused, bridged or spirocyclic ring. Examples of (C3-C13)-cycloalkyl cyclic alkyl residues are cycloalkyl residues containing 3, 4, 5, 6, 7, 8, 9, 10, 11, 12 or 13 ring carbon atoms like cyclopropyl, cyclobutyl, cyclopentyl, cyclohexyl, cycloheptyl, cyclooctyl, cyclononyl, cyclodecyl, cycloundecyl or cyclododecyl. The term cycloalkyl also includes bicyclic groups in which any of the above cycloalkyl ring is fused to a benzene ring, for example indane and 1,2,3,4-tetrahydronaphthalene.

The term cycloalkenyl is to be understood to mean unsaturated hydrocarbon cycle containing from 3 to 8 carbon atoms in a mono- or bicyclic, fused or bridged ring, wherein the one, two or three double bonds are not located within a cyclic alkyl group in such a manner that an aromatic system results. Examples of unsaturated cycloalkenyl groups are cyclopentenyl or cyclohexenyl, which can be bonded via any carbon atom. The term cycloalkenyl also includes bicyclic groups in which any of the above cycloalkenyl ring is fused to a benzene ring, for example 1,2-dihydronaphthalene, 1,4-dihydronaphthalene and 1H-indene.

If not otherwise defined cycloalkyl or cycloalkenyl are unsubstituted or mono-, di- or trisubstituted independently of one another by suitable groups such as, for example: F, Cl, Br, I, CF3, NO2, CN, COOH, CO—O—(C0-04)alkylene-(C6-C10)aryl, CO—O—(C1-C4)alkyl, CO—O—(C0-C4)alkylene-(C3-C13)cycloalkyl, CO—O—(C0-C4)alkylene-(C3-C15)heterocycle, CO—N((C0-C4)alkylene-H)—(C1-C6)

alkylene-H, CO—N((C0-C4)alkylene-H)—(C1-C6)cycloalkyl, CON((C0-C4)alkylene-H)—(C0-C4)alkylene-(C6-C12)-aryl, (C0-C4)alkylene-(C3-C6)cycloalkyl, (C3-C6)alkyl, (C2-C6)-alkenyl, (C2-C6)-alkinyl, (C0-C4)alkylene-(C6-C10)aryl, (C0-C4)alkylene-(C3-C15)heterocycle, O—(C0-C6)-alkyl, (C0-C4)alkylene-O—(C0-C4)alkyl, (C0-C4)alkylene-O—(C0-C4)alkylene-(C3-C13)cycloalkyl, (C0-C4)alkylene-O—(C0-C4)alkylene-(C6-C10)aryl, (C0-C4)alkylene-O—(C0-C4)alkylene-(C3-C15)heterocycle, O—CO—O—(C0-C4)alkylene-(C6-C10)aryl, O—CO—O—(C1-C4)alkyl, O—CO—O—(C0-C4)alkylene-(C3-C13)cycloalkyl, O—CO—O—(C0-C4)alkylene-(C3-C15)heterocycle, O—CO—N((C0-C4)alkylene-H)—(C0-C4)alkylene-(C6-C10)aryl, O—CO—N((C0-C4)alkylene-H)—(C0-C4)alkylene-H, O—CO—N((C0-C4)alkylene-H)—(C0-C4)alkylene-(C3-C13)cycloalkyl, O—CO—N((C0-C4)alkylene-H)—(C0-C4)alkylene-(C3-C15)heterocycle, S—(C1-C4)alkyl, S—(C0-C4)alkylene-(C3-C13)cycloalkyl, S—(C0-C4)alkylene-(C6-C10)aryl, S—(C0-C4)alkylene-(C3-C15)heterocycle, SO—(C1-C4)alkyl, SO—(C0-C4)alkylene-(C3-C13)cycloalkyl, SO—(C0-C4)alkylene-(C6-C10)aryl, SO—(C0-C4)alkylene-(C3-C15)heterocycle, SO2-(C1-C4)alkyl, SO2-(C0-C4)alkylene-(C3-C13)cycloalkyl, SO2-(C0-C4)alkylene-(C6-C10)aryl, SO2-(C0-C4)alkylene-(C3-C15)heterocycle, SO2-N((C0-C4)alkylene-H)—(C0-C4)alkylene-(C6-C10)aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15)heterocycle, where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H; N((C0-C4)-alkylene-H)—(C0-C4)-alkylene-H, N((C0-C4)alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4) alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "aryl" is understood to mean aromatic hydrocarbon ring containing from 6 to 14 carbon atoms in a mono- or bicyclic ring. Examples of (C6-C14)-aryl rings are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl rings, naphthyl ringand, in particular, phenyl ringare further embodiments of aryl ring.

The terms heterocycle is understood to mean saturated (heterocycloalkyl), partly unsaturated (heterocycloalkenyl) or unsaturated (heteroaryl)hydrocarbon rings containing from 3 to 15 carbon atoms in a mono- or bicyclic, fused, bridged or spirocyclicring in which 1 to 5 carbon atoms of the 3 to 15 ring carbon atoms are replaced by heteroatoms such as nitrogen, oxygen or sulfur in which further the heteroatoms can be oxidized, for example N=O, S=O, SO2. Examples of heterocycles are acridinyl, azaindole (1H-pyrrolopyridinyl), azabenzimidazolyl, azaspirodecanyl, azepinyl, azetidinyl, aziridinyl, benzimidazolyl, benzofuranyl, dihydrobenzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The heterocyclic rings are unsubstituted or mono-, di- or trisubstituted by suitable groups such as, for example: F, Cl, Br, I, CF3, NO2, CN, COOH, CO—O—(C0-C4)alkylene-(C6-C10)aryl, CO—O—(C1-C4)alkyl, CO—O—(C0-C4)alkylene-(C3-C13)cycloalkyl, CO—O—(C0-C4)alkylene-(C3-C15)heterocycle, CO—N((C0-C4)alkylene-H)—(C1-C6)alkylene-H, CO—N((C0-C4)alkylene-H)—(C1-C6)cycloalkyl, CON((C0-C4)alkylene-H)—(C0-C4)alkylene-(C6-C12)-aryl, (C0-C4)alkylene-(C3-C6)cycloalkyl, (C3-C6)alkyl, (C2-C6)-alkenyl, (C2-C6)-alkinyl, (C0-C4)alkylene-(C6-C10)aryl, (C0-C4)alkylene-(C3-C15)heterocycle, O—(C0-C6)-alkyl, (C0-C4)alkylene-O—(C0-C4)alkyl, (C0-C4)alkylene-O—(C0-C4)alkylene-(C3-C13)cycloalkyl, (C0-C4)alkylene-O—(C0-C4)alkylene-(C6-C10)aryl, (C0-C4)alkylene-O—(C0-C4)alkylene-(C3-C15)heterocycle, O—CO—O—(C0-C4)alkylene-(C6-C10)aryl, O—CO—O—(C1-C4)alkyl, O—CO—O—(C0-C4)alkylene-(C3-C13)cycloalkyl, O—CO—O—(C0-C4)alkylene-(C3-C15)heterocycle, O—CO—N((C0-C4)alkylene-H)—(C0-C4)alkylene-(C6-C10)aryl, O—CO—N((C0-C4)alkylene-H)—(C0-C4)alkylene-H, O—CO—N((C0-C4)alkylene-H)—(C0-C4)alkylene-(C3-C13)cycloalkyl, O—CO—N((C0-C4)alkylene-H)—(C0-C4)alkylene-(C3-C15)heterocycle, S—(C1-C4)alkyl, S—(C0-C4)alkylene-(C3-C13)cycloalkyl, S—(C0-C4)alkylene-(C6-C10)aryl, S—(C0-C4)alkylene-(C3-C15)heterocycle, SO—(C1-C4)alkyl, SO—(C0-C4)alkylene-(C3-C13)cycloalkyl, SO—(C0-C4)alkylene-(C6-C10)aryl, SO—(C0-C4)alkylene-(C3-C15)heterocycle, SO2-(C1-C4)alkyl, SO2-(C0-C4)alkylene-(C3-C13)cycloalkyl, SO2-(C0-C4)alkylene-(C6-C10)aryl, SO2-(C0-C4)alkylene-(C3-C15)heterocycle, SO2-N((C0-C4)alkylene-H)—(C0-C4)alkylene-(C6-C10)aryl, SO2-N((C0-C4)alkylene-H)—(C0-C4)alkylene-H, SO2-N((C0-C4)alkylene-H)—(C0-C4)alkylene-(C3-C13)cycloalkyl, SO2-N((C0-C4)alkylene-H)—(C0-C4)alkylene-(C3-C15)heterocycle, where the aryl ring or heterocyclic ring is unsubstituted or mono- or disubstituted by F, Cl, Br, OH, CF3, NO2, CN, OCF3, O—(C1-C6)-alkyl, (C1-C6)-alkyl, N((C0-C4)-alkylene-H)—(C0-C4)-alkylene-H;

N((C0-C4)-alkylene-H)—(C0-C4)-alkylene-H, N((C0-C4)alkylene-H)—(C0-C4)alkylene-H)—(C1-C6)cycloalkyl, N((C0-C4)alkylene-H)—(C0-C4)alkylene-(C6-C12)-aryl, N((C0-C4)alkylene-H)—(C0-C4)alkylene-(C3-C15)heterocycle, N((C0-C4)alkylene-H)—CO—(C0-C4)alkylene-(C6-C12)-aryl, N((C0-C4)alkylene-H)—CO—(C0-C4)alkyl, N((C0-C4)alkylene-H)—CO—(C0-C4)alkylene-(C3-C13)cycloalkyl, N((C0-C4)alkylene-H)—CO—(C0-C4)alkylene-(C3-C15)heterocycle, N((C0-C4)alkylene-H)—CO—O—(C0-C4)alkylene-(C6-C12)-aryl, N((C0-C4)alkylene-H)—CO—O—(C0-C4)alkyl, N((C0-C4)alkylene-H)—CO—O—(C0-C4)alkylene-(C3-C13)cycloalkyl, N((C0-C4)alkylene-H)—CO—O—(C0-C4)alkylene-(C3-C15)heterocycle, N((C0-C4)alkylene-H)—CO—N((C0-C4)-alkylene-H)—(C0-C4)alkylene-(C6-C12)-aryl, N((C0-C4)alkylene-H)—CO—N((C0-C4)-alkylene-H)—(C0-C4)alkyl, N((C0-C4)alkylene-H)—CO—N((C0-C4)-alkylene-H)—(C0-C4)alkylene-(C3-C13)cycloalkyl, N((C0-C4)alkylene-H)—CO—N((C0-C4)-alkylene-H)—(C0-C4)alkylene-(C3-C15)heterocycle, where the aryl or heterocyclic ring is unsubstituted or mono- or disubstituted by F, Cl, Br, I, OH, CF3, NO2, CN, OCF3, O—(C1-C6)-alkyl, (C1-C6)-alkyl, N((C0-C4)-alkylene-H)—(C0-C4)-alkylene-H, SO2-CH3, COOH, COO—(C1-C6)-alkyl, SF5, CONH2.

The term "oxo-residue" or "=O" refers to residues such as carbonyl (—CO—), nitroso (—N=O), sulfinyl (—SO— or sulfonyl (—SO$_2$—).

Halogen is fluorine, chlorine, bromine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The compounds of the formula I may exist in the form of their racemates, racemic mixtures, pure enantiomers, diastereomers and mixtures of diastereomers as well in their tautomeric forms. The present invention encompasses all these isomeric and tautomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

This invention relates further to the use of compounds of the formula I and their pharmaceutical compositions as PPAR ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta (identical to PPARbeta), which are encoded by different genes (Peroxisome proliferator-activated receptor (PPAR):

structure, mechanisms of activation and diverse functions: Motojima K., Cell Struct Funct., 1993, 18(5), 267-77).

In humans, PPARgamma exists in three variants, PPAR-gamma$_1$, gamma$_2$, and gamma$_3$, which are the result of alternative use of promoters and differential mRNA splicing. Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, the PPARalpha receptor plays an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effects and pathophysiology, see: Berger, J. et al., Annu. Rev. Med., 2002, 53, 409-435; Wilson, T. et al., J. Med. Chem., 2000, 43 (4), 527-550; Kliewer, S. et al., Recent Prog Norm Res., 2001, 56, 239-63; Moller, D. E. and Berger, J. P., Int J Obes Relat Metab Disord., 2003, 27 Suppl 3, 17-21; Ram, V. J., Drugs Today, 2003, 39(8), 609-32).

Among the three PPAR-isoforms the physiological functions of PPARdelta have long remained an enigma. The first proposed pharmacological role for PPARdelta has been the regulation of cholesterol homeostasis. It was shown that the somewhat selective PPARdelta ligand L-165041 raises plasma cholesterol in a diabetic animal model (Berger J. et al., J. Biol. Chem., 1999, 274, 6718-6725; Leibowitz M. D. et al., FEBS Lett., 2000, 473(3), 333-336). In obese, insulin resistant rhesus monkeys, the potent and selective PPARdelta ligand GW501516 raises HDL-cholesterol, decreases plasma LDL-cholesterol, triglycerides and insulin levels (Oliver, W. et al., Proc. Natl. Acad. Sci., 2001, 98, 5306-5311). The dual PPARdelta/PPARalpha agonist YM-16638 significantly lowers plasma lipids in rhesus and cynomolgus monkeys (Goto, S. et al., Br. J. Pharm., 1996, 118, 174-178) and acts in a similar manner in two weeks clinical trials in healthy volunteers (Shimokawa, T. et al., Drug Dev. Res., 1996, 38, 86-92). More recent publications underline that PPARdelta is an important target for the treatment of dyslipidemia, insulin resistance, type 2 diabetes, atherosclerosis and syndrom X (Wang, Y-X. et al., Cell, 2003, 113, 159-170; Luquet, S. et al., FASEB J., 2003, 17, 209-226; Tanaka, T. et al., PNAS, 2003, 100, 15924-15929; Holst, D. et al., BioChem. Biophys. Acta, 2003, 1633, 43-50; Dressel, U. et al., Mol. Endocrin., 2003, 17, 2477-2493; Lee, C. H. et al., Science, 2003, 302, 453-457).

Besides its actions as a regulator of the lipid-, glucose- and cholesterol-metabolism PPARdelta is known to play a role in embryonic development, implantation and bone formation (Lim, H. and Dey, S. K., Trends Endocrinol Metab., 2000, 11(4), 137-42; Ding, N. Z. et al., Mol Reprod Dev., 2003, 66(3), 218-24; Mano, H. et al., J Biol. Chem., 2000, 275(11), 8126-32).

Numerous publications demonstrate that PPARdelta is triggering proliferation and differentiation of keratinocytes which points to its role in skin disorders and wound healing (Di-Poi, N. et al., J Steroid Biochem Mol. Biol., 2003, 85(2-5), 257-65; Tan, N. S. et al., Am J Clin Dermatol., 2003, 4(8), 523-30; Wahli, W., Swiss Med. Wkly., 2002, 132(7-8), 83-91).

PPARdelta appears to be significantly expressed in the CNS; however much of its function there still remains undiscovered. Of singular interest however, is the discovery that PPARdelta was expressed in rodent oligodendrocytes, the major lipid producing cells of the CNS (J. Granneman, et al., J. Neurosci. Res., 1998, 51, 563-573). Moreover, it was also found that a PPARdelta selective agonist was found to significantly increase oligodendroglial myelin gene expression and myelin sheath diameter in mouse cultures (I. Saluja et al., Glia, 2001, 33, 194-204). Thus, PPARdelta activators may be of use for the treatment of demyelinating and dysmyelinating diseases. The use of peroxisome proliferator activated receptor delta agonists for the treatment of MS and other demyelinating diseases can be shown as described in WO2005/097098.

Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, Demyelinating Diseases. In Greenfield's Neuropathology, 6.sup.th ed. (Edward Arnold: New York, 1997) 813-811, Beers and Berkow, eds., The Merck Manual of Diagnosis and Therapy, 17.sup.th ed. (Whitehouse Station, N.J.: Merck Research Laboratories, 1999) 1299, 1437, 1473-76, 1483).

Central demyelination (demyelination of the CNS) occurs in several conditions, often of uncertain etiology, that have come to be known as the primary demyelinating diseases. Of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillian-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Also, disorders in which myelin forming glial cells are damaged including spinal cord injuries, neuropathies and nerve injury.

The present invention relates to compounds of the formula I suitable for modulating the activity of PPARs, especially the activity of PPARdelta and PPARalpha. Depending on the modulation profile, the compounds of the formula I are suitable for the treatment, control and prophylaxis of the indications described hereinafter, and for a number of other pharmaceutical applications connected thereto (see, for example, Berger, J., et al., Annu. Rev. Med., 2002, 53, 409-435; Wilson, T. et al., J. Med. Chem., 2000, 43(4), 527-550; Kliewer, S. et al., Recent Prog Horm Res., 2001, 56, 239-63; Fruchart, J. C. et al., 2001, Pharmacological Research, 44(5), 345-52; Kersten, S. et al., Nature, 2000, 405, 421-424; Torra, I. P. et al., Curr Opin Lipidol, 2001, 12, 245-254).

Compounds of this type are particularly suitable for the treatment and/or prevention of:
1. Disorders of fatty acid metabolism and glucose utilization disorders.
   Disorders in which insulin resistance is involved
2. Diabetes mellitus, especially type 2 diabetes, including the prevention of the sequelae associated therewith.
   Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Disorders or conditions in which inflammatory reactions are involved:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   asthma
   lupus erythematosus (LE) or inflammatory rheumatic disorders such as, for example, rheumatoid arthritis
   other inflammatory states
6. Disorders of cell cycle or cell differentiation processes:
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis
7. Demyelinating and other neurodegenerative disorders of the central and peripheral nervous systems including:
   Alzheimer's disease
   multiple sclerosis
   Parkinson's disease
   adrenoleukodystrophy (ALD)
   adrenomyeloneuropathy
   AIDS-vacuolar myelopathy
   HTLV-associated myelopathy
   Leber's hereditary optic atrophy
   progressive multifocal leukoencephalopathy (PML)
   subacute sclerosing panencephalitis
   Guillian-Barre syndrome
   tropical spastic paraparesis
   acute disseminated encephalomyelitis (ADEM)
   acute viral encephalitis
   acute transverse myelitis
   spinal cord and brain trauma
   Charcot-Marie-Tooth disease
8. Skin disorders and/or disorders of wound healing processes:
   erythemato-squamous dermatoses such as, for example, psoriasis
   acne vulgaris
   other skin disorders and dermatological conditions which are modulated by PPAR
   eczemas and neurodermitis
   dermatitis such as, for example, seborrheic dermatitis or photodermatitis
   keratitis and keratoses such as, for example, seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections such as, for example, venereal papillomata, viral warts such as, for example, molluscum contagiosum, leukoplakia
   papular dermatoses such as, for example, Lichen planus
   skin cancer such as, for example, basal-cell carcinomas, melanomas or cutaneous T-cell lymphomas
   localized benign epidermal tumors such as, for example, keratoderma, epidermal naevi
   chilblains
   wound healing
9. Other disorders
   high blood pressure
   pancreatitis
   syndrome X
   polycystic ovary syndrome (PCOS)
   asthma
   osteoarthritis
   lupus erythematosus (LE) or inflammatory rheumatic disorders such as, for example, rheumatoid arthritis
   vasculitis
   wasting (cachexia)
   gout
   ischemia/reperfusion syndrome
   acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and atheriosclerosis and the diverse sequalae thereof.

Combinations with Other Medicaments

The compounds of the invention can be administered alone or in combination with one or more further pharmacologically active substances. In particular, the compounds of the invention can be administered in combination with active ingredients having a similar pharmacological action. For example, they can be administered in combination with active ingredients which have favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.
11. active ingredients for the treatment of neurodegenerative diseases
12. active ingredients for the treatment of disorders of the central nervous system
13. active ingredients for the treatment of drug, nicotine and alcohol addiction
14. analgesics They can be combined with the compounds of the invention of the formula I in particular for a synergistic enhancement of activity. Administration of the active ingredient combination can take place either by separate administration of the active ingredients to the patient or in the form of combination products in which a plurality of active ingredients are present in one pharmaceutical preparation.

Further active ingredients suitable for combination products are:

All antidiabetics which are mentioned in the Rote Liste 2005, chapter 12; all weight-reducing agents/appetite suppressants which are mentioned in the Rote Liste 2005, chapter 1; all lipid-lowering agents which are mentioned in the Rote Liste 2005, chapter 58. They may be combined with the compound of the invention of the formula I in particular for a synergistic improvement in the effect. The active ingredient combination can be administered either by separate administration of the active ingredients to the patient or in the form of combination products in which a plurality of active ingredients is present in a pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, LANTUS® (see www.lantus.com) or HMR 1964 or LEVEMIR® (insulin detemir) or those described in WO2005005477 (Novo Nordisk), fast-acting insulins (see U.S. Pat. No. 6,221,633), inhalable insulins such as, for example, EXUBERA® or oral insulins such as, for example, IN-105 (Nobex) or ORAL-LYN™ (Generex Biotechnology), GLP-1 derivatives and GLP-1 agonists such as, for example, exenatide, liraglutide or those which have been disclosed in WO98/08871, WO2005027978, WO2006037811 or WO2006037810 of Novo Nordisk A/S, in WO01/04156 of Zealand or in WO00/34331 of Beaufour-Ipsen, pramlintide acetate (Symlin; Amylin Pharmaceuticals), BIM-51077, PC-DAC-exendin-4 (an exendin-4 analog covalently bonded to recombinant human albumin), agonists like those described for example in D. Chen et al., Proc. Natl. Acad. Sci. USA 104 (2007) 943, those as are described in WO2006124529, and orally effective hypoglycemic active ingredients.

Antidiabetics also include agonists of the glucose-dependent insulinotropic polypeptide (GIP) receptor as are described for example in WO2006121860.

The orally effective hypoglycemic active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT),
GLP-1 agonists,
potassium channel openers such as, for example, pinacidil, cromakalim, diazoxide or those described in R. D. Carr et al., Diabetes 52, 2003, 2513.2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compounds of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.), or WO2005044256 or WO2005062824 (Merck & Co.) or WO2005061451 and WO2005061452 (AstraZeneca AB), and WO2006017257 (Phenomix) or WO2005033100 (Lipideon Biotechnology AG), or as described in WO2004097655, WO2004000805, WO2004000804, WO2004000803, WO2002050068, WO2002050060, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163.

In one embodiment of the invention, the compound of the formula I is administered in combination with VYTORIN™, a fixed combination of ezetimibe and simvastatin.

In one embodiment of the invention, the compound of the formula I is administered in combination with a fixed combination of ezetimibe with atorvastatin.

In one embodiment of the invention, the compound of the formula I is administered in combination with a fixed combination of ezetimibe with fenofibrate.

In a further embodiment of the invention, the compound of the formula I is administered in combination with a fixed combination of fenofibrate and rosuvastatin.

In one embodiment of the invention, the compound of the formula I is administered in combination with SYNORDIA®, a fixed combination of fenofibrate with metformin.

In one embodiment of the invention, the compound of the formula I is administered in combination with ISIS-301012, an antisense oligonucleotide able to regulate the apolipoprotein B gene.

In one embodiment of the invention, the compound of the formula I is administered in combination with a PPAR gamma agonist such as, for example, rosiglitazone, pioglitazone, JTT-501, GI 262570, R-483, CS-011 (rivoglitazone).

In one embodiment of the invention, the compound of the formula I is administered in combination with COMPETACT™, a fixed combination of pioglitazone hydrochloride with metformin hydrochloride.

In one embodiment of the invention, the compound of the formula I is administered in combination with TANDEMACT™, a fixed combination of pioglitazone with glimepiride.

In one embodiment of the invention, the compound of the formula I is administered in combination with a fixed combination of pioglitazone hydrochloride with an angiotensin II agonist such as, for example, TAK-536.

In one embodiment of the invention, the compound of the formula I is administered in combination with a PPAR alpha agonist such as, for example, GW9578, GW-590735, K-111, LY-674, KRP-101, DRF-10945, LY-518674 or those as are described in WO2001040207, WO2002096894, WO2005097076.

In one embodiment of the invention, the compound of the formula I is administered in combination with a mixed PPAR alpha/gamma agonist such as, for example, naveglitazar, LY-510929, ONO-5129, E-3030, AVE 8042, AVE 8134, AVE 0847, CKD-501 (lobeglitazone sulfate) or as described in WO 00/64888, WO 00/64876, WO03/020269 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516 or as described in WO2006059744, WO2006084176, WO2006029699, WO2007039172-WO2007039178.

In one embodiment, the compound of the formula I is administered in combination with metaglidasen or with MBX-2044 or other partial PPAR gamma agonists/antagonists.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757, AS-1552133 or those described in WO2005085226, WO2005121091, WO2006010423.

In one embodiment of the invention, the compound of the formula I is administered in combination with a CETP inhibitor such as, for example, torcetrapib or JTT-705 or those described in WO2006002342, WO2006010422, WO2006012093, WO2006073973, WO2006072362, WO2006097169, WO2007041494.

In one embodiment of the invention, the compound of the formula I is administered in combination with a bile acid absorption inhibitor (see, for example, U.S. Pat. Nos. 6,245, 744, 6,221,897 or WO00/61568), such as, for example, HMR 1741 or those as described in DE 10 2005 033099.1 and DE 10 2005 033100.9, WO2007009655-56.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO2005097738.

In one embodiment of the invention, the compound of the formula I is administered in combination with an ABCA1 expression enhancer as described for example in WO2006072393.

In a further embodiment of the invention, the compound of the formula I is administered in combination with an RNAi therapeutic directed against PCSK9 (proprotein convertase subtilisin/kexin type 9).

In one embodiment, the compound of the formula I is administered in combination with OMACOR® (omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe or SMP-797.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494, TAK-475 or as described in WO2005077907, JP2007022943.

In one embodiment of the invention, the compound of the formula I is administered in combination with a lipoprotein (a) antagonist such as, for example, gemcabene (CI-1027).

In one embodiment of the invention, the compound of the formula I is administered in combination with an agonist of GPR109A (HM74A receptor agonist; NAR agonist (nicotinic acid receptor agonist) such as, for example, nicotinic acid or extended release niacin in conjunction with MK-0524A or those compounds described in WO2006045565, WO2006045564, WO2006069242, WO2006124490, WO2006113150, WO2007017261, WO2007017262, WO2007017265, WO2007015744, WO2007027532.

In another embodiment of the invention, the compound of the formula I is administered in combination with an agonist of GPR116 as are described for example in WO2006067531, WO2006067532.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment, the compound of the formula I is administered in combination with a sulfonylurea such as, for example, tolbutamide, glibenclamide, glipizide, gliclazide or glimepiride.

In one embodiment, the compound of the formula I is administered in combination with a substance which enhances insulin secretion, such as, for example, KCP-265 (WO2003097064) or those described in WO2007026761.

In one embodiment, the compound of the formula I is administered in combination with agonists of the glucose-dependent insulinotropic receptor (GDIR) such as, for example, APD-668.

In one embodiment, the compound of the formula I is administered in combination with a biguanide such as, for example, metformin.

In yet another embodiment, the compound of the formula I is administered in combination with a meglitinide such as, for example, repaglinide, nateglinide or mitiglinide In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In one embodiment, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]-phenyl]methyl]-2,4-thiazolidinedione.

In one embodiment, the compound of the formula I is administered in combination with an α-glucosidase inhibitor such as, for example, miglitol or acarbose.

In one embodiment, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, such as, for example, PSN-357 or FR-258900 or those as described in WO2003084922, WO2004007455, WO2005073229-31 or WO2005067932.

In one embodiment, the compound of the formula I is administered in combination with glucagon receptor antagonists such as, for example, A-770077, NNC-25-2504 or as described in WO2004100875 or WO2005065680.

In one embodiment, the compound of the formula I is administered in combination with activators of glucokinase, such as, for example, LY-2121260 (WO2004063179), PSN-105, PSN-110, GKA-50 or those as are described for example in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847.

In one embodiment, the compound of the formula I is administered in combination with an inhibitor of gluconeogenesis, such as, for example, FR-225654.

In one embodiment, the compound of the formula I is administered in combination with inhibitors of fructose-1,6-bisphosphatase (FBPase), such as, for example, CS-917 (MB-06322) or MB-07803 or those described in WO2006023515, WO2006104030, WO2007014619.

In one embodiment, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, the compound of the formula I is administered in combination with inhibitors of glutamine-fructose-6-phosphate amidotransferase (GFAT), as are described for example in WO2004101528.

In one embodiment, the compound of the formula I is administered in combination with inhibitors of dipeptidylpeptidase IV (DPP-IV), such as, for example, vildagliptin (LAF-237), sitagliptin (MK-0431), sitagliptin phosphate, saxagliptin ((BMS-477118), GSK-823093, PSN-9301, SYR-322, SYR-619, TA-6666, TS-021, GRC-8200, GW-825964X, KRP-104, DP-893, ABT-341, ABT-279 or another salt thereof or those compounds as are described in WO2003074500, WO2003106456, WO2004037169, WO200450658, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006090915, WO2006104356, WO2006127530, WO2006111261, WO2007015767, WO2007024993, WO2007029086.

In one embodiment, the compound of the formula I is administered in combination with JANUMET™, a fixed combination of sitagliptin phosphate with metformin hydrochloride.

In one embodiment, the compound of the formula I is administered in combination with inhibitors of 11-beta-hydroxysteroid dehydrogenase 1 (11β-HSD1), such as, for example, BVT-2733, JNJ-25918646, INCB-13739 or those as are described for example in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138695, WO2006133926, WO2007003521, WO2007007688, US2007066584, WO2007047625, WO2007051811, WO2007051810.

In one embodiment, the compound of the formula I is administered in combination with inhibitors of protein tyrosine phosphatase 1B (PTP1B), as are described for example in WO200119830-31, WO200117516, WO2004506446, WO2005012295, WO2005116003, WO2005116003, WO2006007959, DE 10 2004 060542.4, WO2007009911, WO2007028145, WO2007081755.

In one embodiment, the compound of the formula I is administered in combination with modulators of the sodium-dependent glucose transporter 1 or 2 (SGLT1, SGLT2), such as, for example, KGA-2727, T-1095, SGL-0010, AVE 2268, SAR 7226 and sergliflozin or as described for example in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170 or by A. L. Handlon in Expert Opin. Ther. Patents (2005) 15(11), 1531-1540.

In one embodiment, the compound of the formula I is administered in combination with modulators of GPR40 as are described for example in WO2007013689, WO2007033002.

In one embodiment, the compound of the formula I is administered in combination with modulators of GPR119b as are described for example in WO2004041274.

In one embodiment, the compound of the formula I is administered in combination with modulators of GPR119 as are described for example in WO2005061489 (PSN-632408), WO2004065380, WO2007003960-62 and WO2007003964.

In a further embodiment, the compound of the formula I is administered in combination with modulators of GPR120.

In one embodiment, the compound of the formula I is administered in combination with inhibitors of hormone-sensitive lipase (HSL) and/or phospholipases as described for example in WO2005073199, WO2006074957, WO2006087309, WO2006111321, WO2007042178.

In one embodiment, the compound of the formula I is administered in combination with inhibitors of acetyl-CoA carboxylase (ACC), such as, for example, those as described in WO199946262, WO200372197, WO2003072197, WO2005044814, WO2005108370, JP2006131559, WO2007011809, WO2007011811, WO2007013691.

In a further embodiment, the compound of the formula I is administered in combination with modulators of xanthine oxidoreductase (XOR).

In one embodiment, the compound of the formula I is administered in combination with an inhibitor of phosphoenolpyruvate carboxykinase (PEPCK), such as, for example, those as described in WO2004074288.

In one embodiment, the compound of the formula I is administered in combination with an inhibitor of glycogen synthase kinase 3 beta (GSK-3 beta), as described for example in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment, the compound of the formula I is administered in combination with an inhibitor of the serum/glucocorticoid-regulated kinase (SGK) as described for example in WO2006072354.

In one embodiment, the compound of the formula I is administered in combination with an agonist of the RUP3 receptor as described for example in WO2007035355.

In one embodiment, the compound of the formula I is administered in combination with an inhibitor of protein kinase C beta (PKC beta), such as, for example, ruboxistaurin.

In another embodiment, the compound of the formula I is administered in combination with an activator of the gene which codes for the ataxia telangiectasia mutated (ATM) protein kinase, such as, for example, chloroquine.

In one embodiment, the compound of the formula I is administered in combination with an endothelin A receptor antagonist such as, for example, avosentan (SPP-301).

In one embodiment, the compound of the formula I is administered in combination with inhibitors of "I-kappaB kinase" (IKK inhibitors), as are described for example in WO2001000610, WO2001030774, WO2004022553 or WO2005097129.

In one embodiment, the compound of the formula I is administered in combination with modulators of the glucocorticoid receptor (GR), as are described for example in WO2005090336, WO2006071609, WO2006135826.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-aminoquinazolin-2-ylamino)methyl] cyclohexylmethyl}amide hydrochloride (CGP 71683A);

NPY-5 receptor antagonists such as L-152804, or as are described for example in WO2006001318;

NPY-4 receptor antagonists as are for example described in WO2007038942;

NPY-2 receptor antagonists as are for example described in WO2007038943;

Peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424, WO2006095166;

derivatives of the peptide obestatin as are described in WO2006096847;

CB1R (cannabinoid receptor 1) antagonists (such as, for example, rimonabant, SR147778, SLV-319, AVE-1625, MK-0364 or salts thereof or those compounds as are described for example in EP 0656354, WO00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007016460, WO2007020502, WO2007026215, WO2007028849, WO2007031720, WO2007031721, WO2007036945, WO2007038045, WO2007039740, US20070015810, WO2007046548, WO2007047737, WO2007084319, WO2007084450); cannabinoid receptor 1/cannabinoid receptor 2 (CB1/CB2) modulating compounds as described for example in WO2007001939, WO2007044215, WO2007047737;

MC4 agonists (e.g. 1-amino-1,2,3,4-tetrahydronaphthalene-2-carboxylic acid [2-(3a-benzyl-2-methyl-3-oxo-2,3,3a,4, 6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052;

orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403, WO2005075458 or WO2006067224);

histamine H3 receptor agonists (e.g. 3-cyclohexyl-1-(4,4-dimethyl-1,4,6,7-tetrahydroimidazo[4,5-c]pyridin-5-yl) propan-1-one oxalic acid salt (WO 00/63208) or those as are described in WO200064884, WO2005082893, WO2006107661, WO2007003804, WO2007016496, WO2007020213);

histamine H1/histamine H3 modulators such as for example betahistine and its dihydrochloride;

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);

urocortin agonists;

agonists of the beta-3 adrenoceptor such as, for example, 1-(4-chloro-3-methanesulfonylmethylphenyl)-2-[2-(2,3-dimethyl-1H-indol-6-yloxy)ethylamino]ethanol hydrochloride (WO 01/83451); or Solabegron (GW-427353) or N-5984 (KRP-204) or those described in JP2006111553, WO2002038543, WO2007048840-843;

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180 or those as are described in WO2005116034);

serotonin reuptake inhibitors (e.g. dexfenfluramine);

mixed serotonin/dopamine reuptake inhibitors (e.g. bupropion) or fixed combinations of bupropion with naltrexone;

mixed sertoninergic and noradrenergic compounds (e.g. WO 00/71549);

5-HT receptor agonists, e.g. 1-(3-ethylbenzofuran-7-yl)piperazine oxalic acid salt (WO 01/09111);

mixed dopamine/norepinephrine/acetylcholine reuptake inhibitors (e.g. tesofensine);

5-HT2C receptor agonists (such as, for example, lorcaserin hydrochloride (APD-356), BVT-933 or those as are described in WO200077010, WO20077001-02, WO2005019180, WO2003064423, WO200242304, WO2005035533, WO2005082859, WO2006077025, WO2006103511);

5-HT6 receptor antagonists such as for example E-6837 or BVT-74316 or those as are described for example in WO2005058858, WO2007054257;

bombesin receptor agonists (BRS-3 agonists);

galanin receptor antagonists;

growth hormone (e.g. human growth hormone or AOD-9604);

growth hormone-releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (see, for example, EP 0 462 884);

uncoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (for example WO 00/40569);

inhibitors of diacylglycerol O-acyltransferases (DGATs) such as, for example, BAY-74-4113 or as described for example in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538;

inhibitors of fatty acid synthase (FAS) such as, for example, C75 or those as described in WO2004005277;

inhibitors of stearoyl-CoA delta9 desaturase (SCD1) as described for example in WO2007009236, WO2007044085, WO2007046867, WO2007046868, WO20070501124;

oxyntomodulin;

oleoyl-estrone or thyroid hormone receptor agonists or partial agonists such as, for example: KB-2115 or those as described in WO20058279, WO200172692, WO200194293, WO2003084915, WO2004018421, WO2005092316, WO2007003419, WO2007009913, WO2007039125.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the SIRT1 enzyme.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, the compound of the formula I is administered in combination with bulking agents, preferably insoluble bulking agents (see, for example, CAROB/CAROMAX® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with CAROMAX® is possible in one preparation or by separate administration of compounds of the formula I and CAROMAX®. CAROMAX® can in this connection also be administered in the form of food products such as, for example, in bakery products or muesli bars.

It will be understood that every suitable combination of the compounds of the invention with one or more of the aforementioned compounds and optionally one or more further pharmacologically active substances will be regarded as falling within the protection conferred by the present invention.

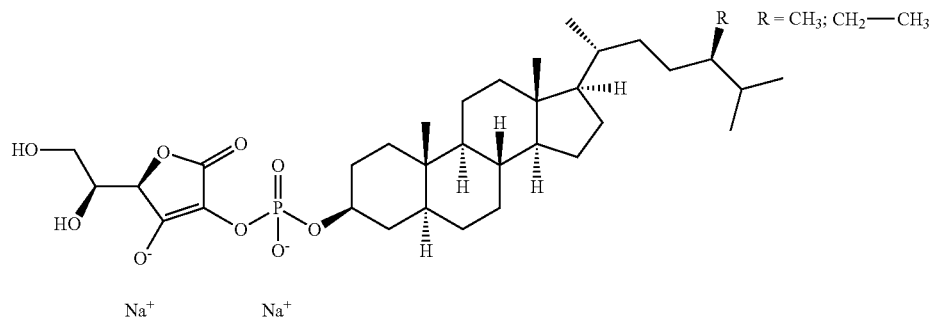

FM-VP4

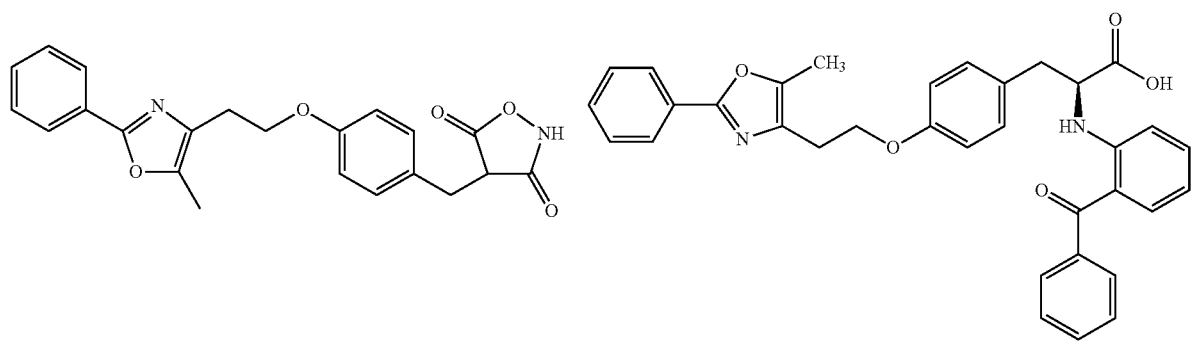

JTT-501

GI 262570

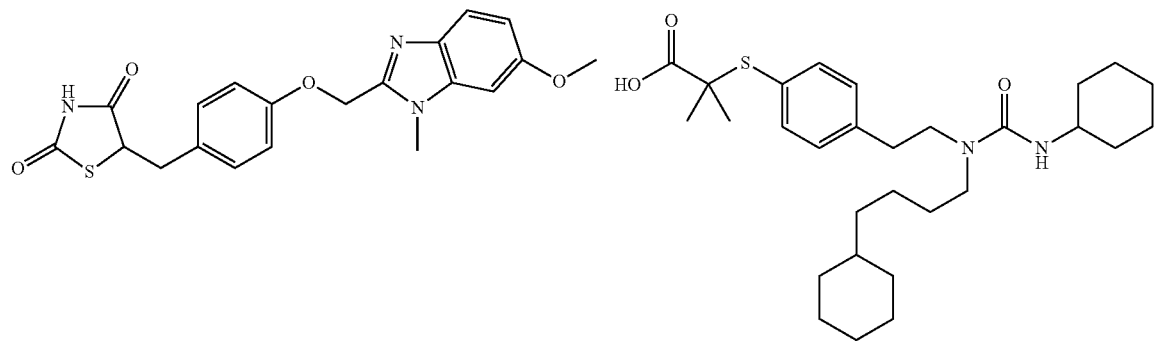

CS-011
Rivoglitazone

GW-9578

-continued
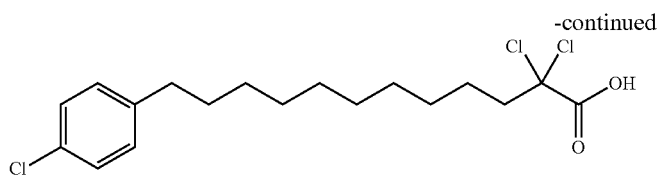
K-111
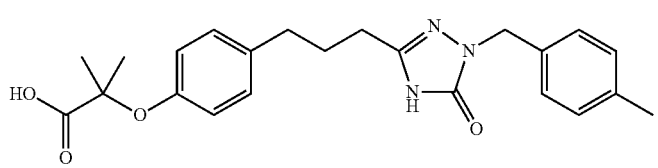
LY-674
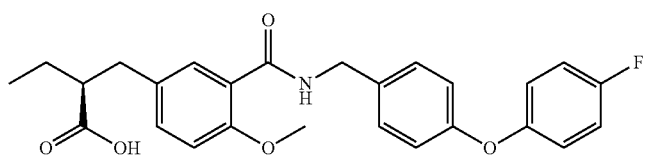
KRP-101
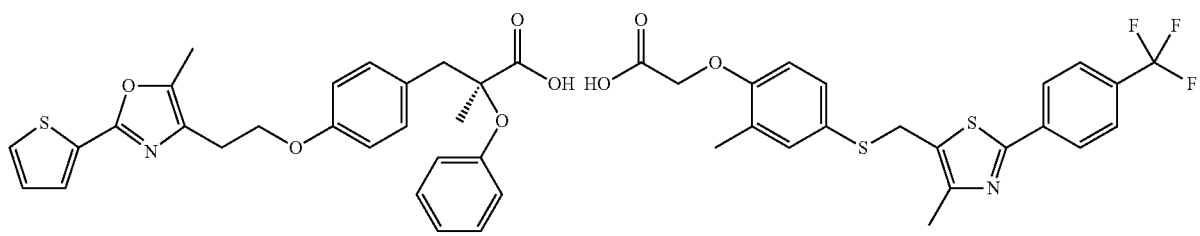
LY-510929  GW-501516
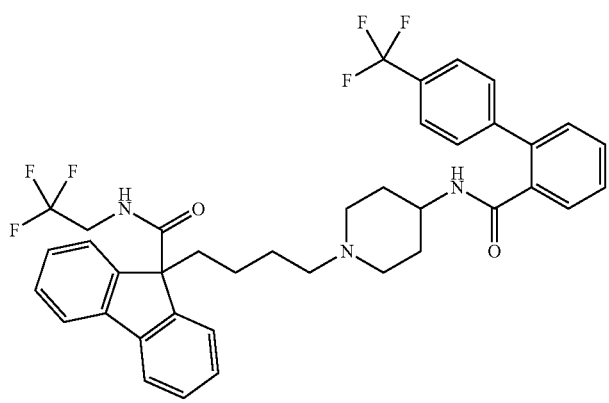
BMS-201038

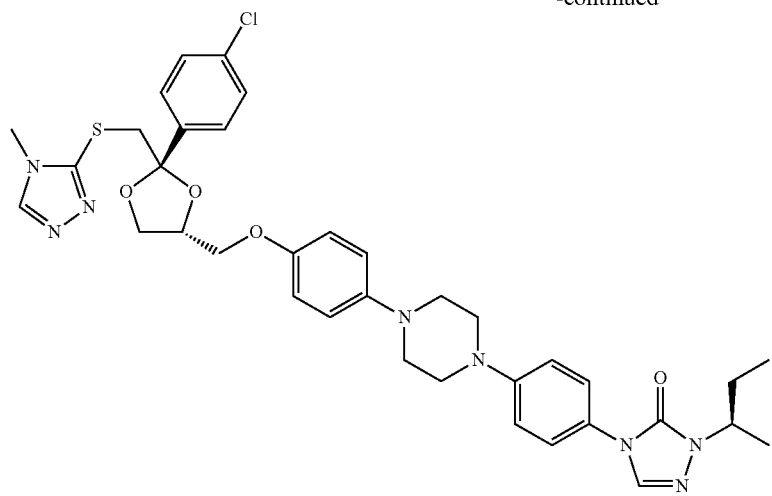
R-103757
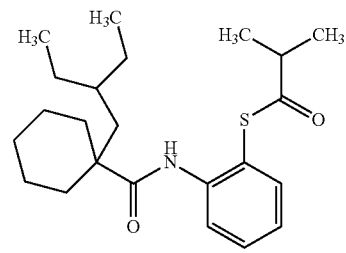
JTT-705
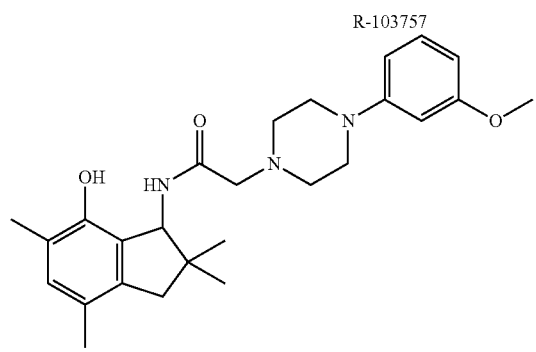
OPC-14117
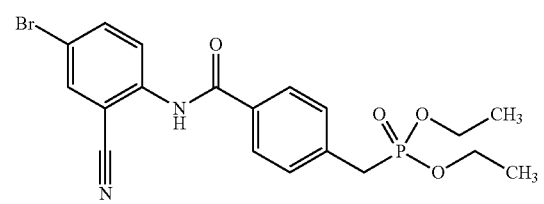
NO-1886
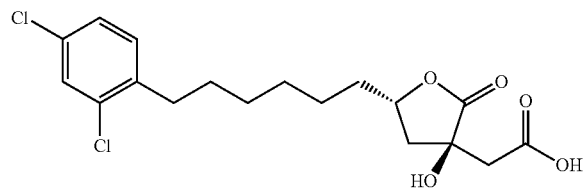
SB-204990
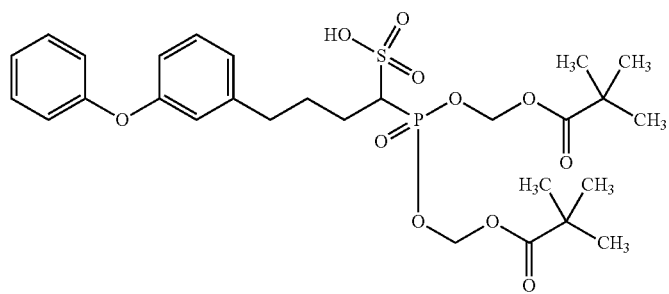
BMS-188494
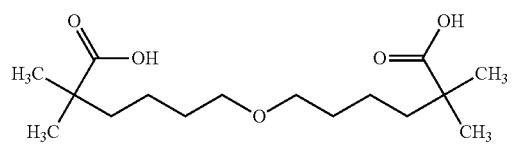
CI-1027
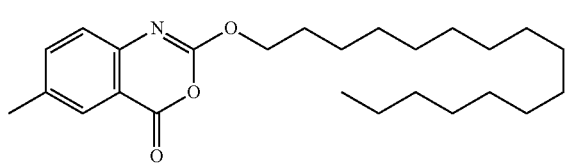
ATL-962

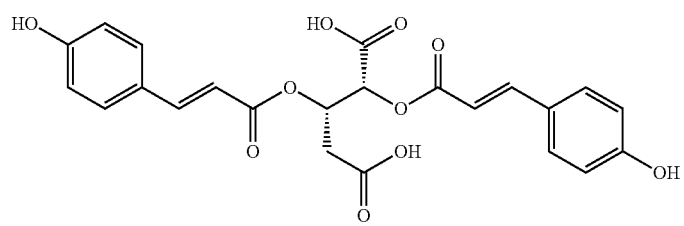
FR-258900
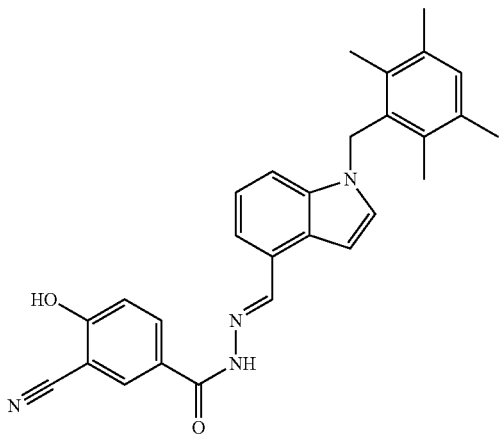
NNC-25-2504
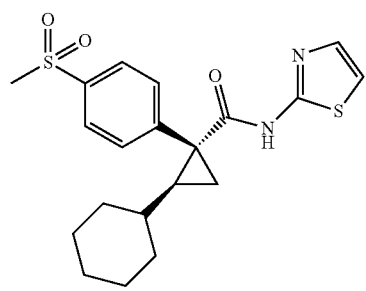
LY-2121260
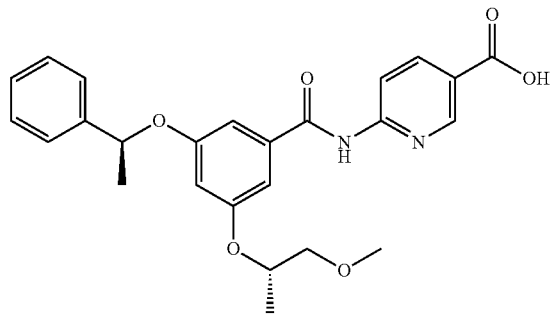
GKA-50
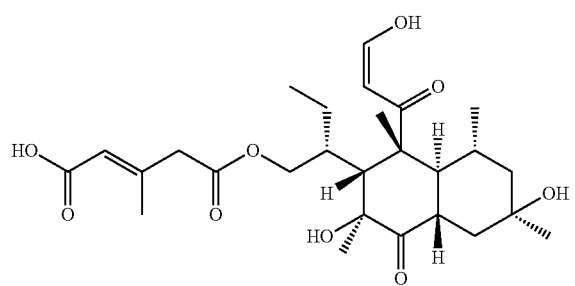
FR-225654
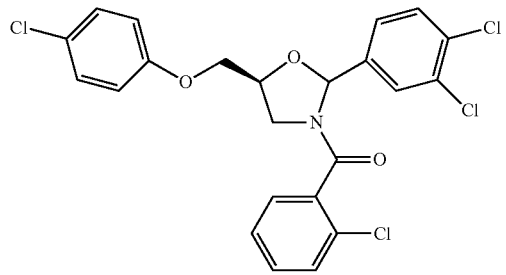
KST-48
H—Cl
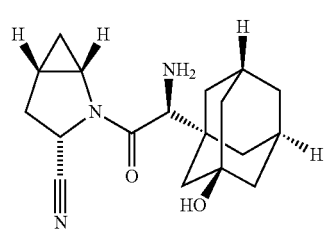
BMS-477118
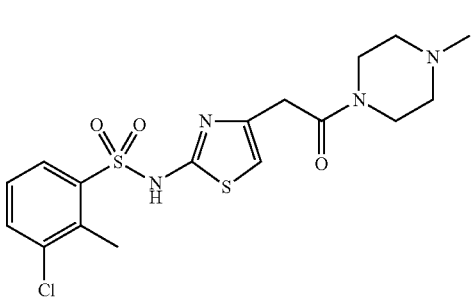
BVT-2733

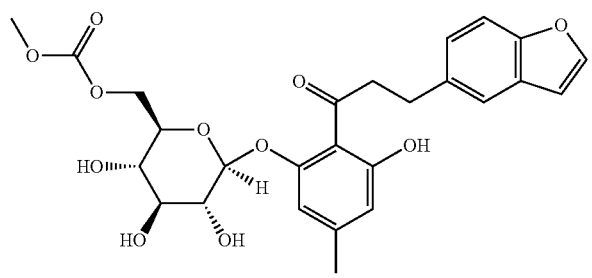
T-1095
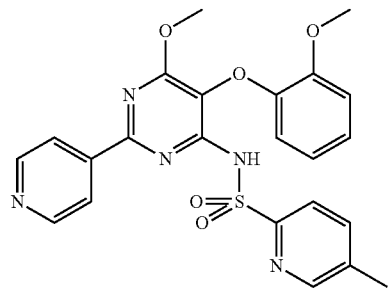
SPP-301
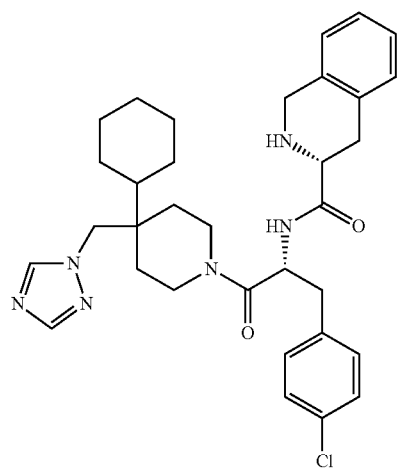
THIQ
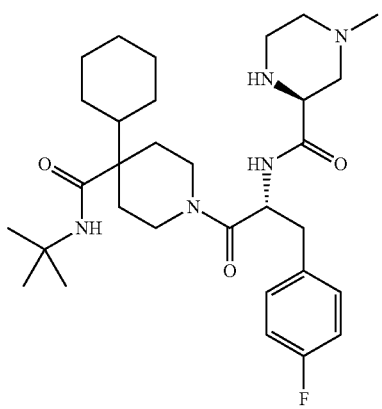
MB243
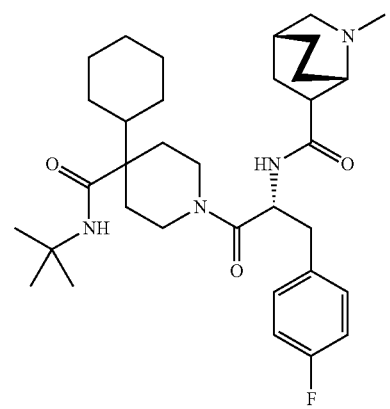
RY764
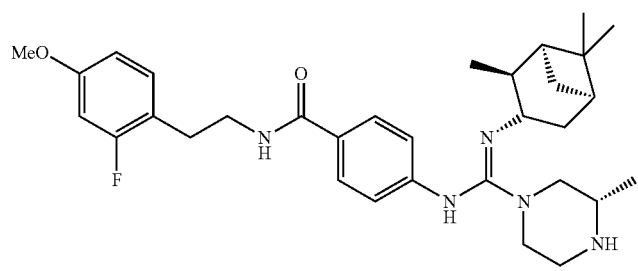
CHIR-785
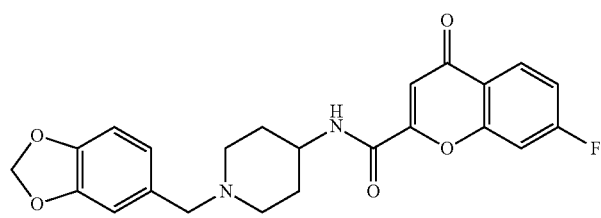
A-761
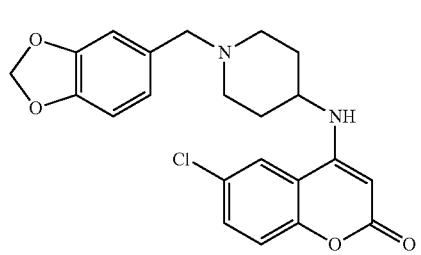
A-665798

37
-continued
38
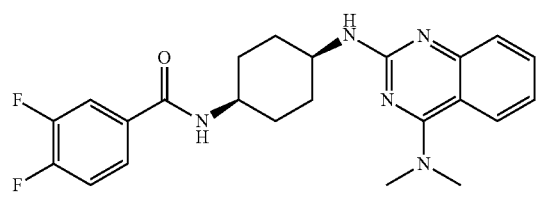
ATC-0175
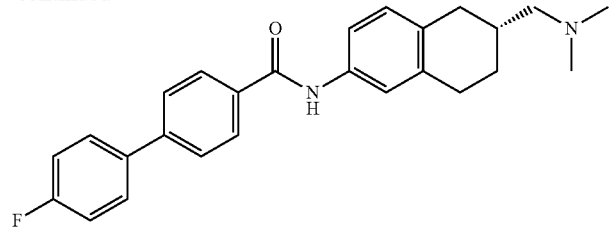
T-226296
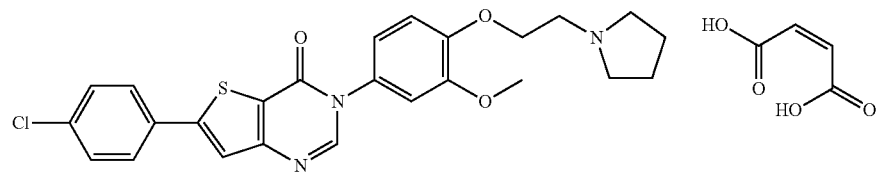
GW-803430
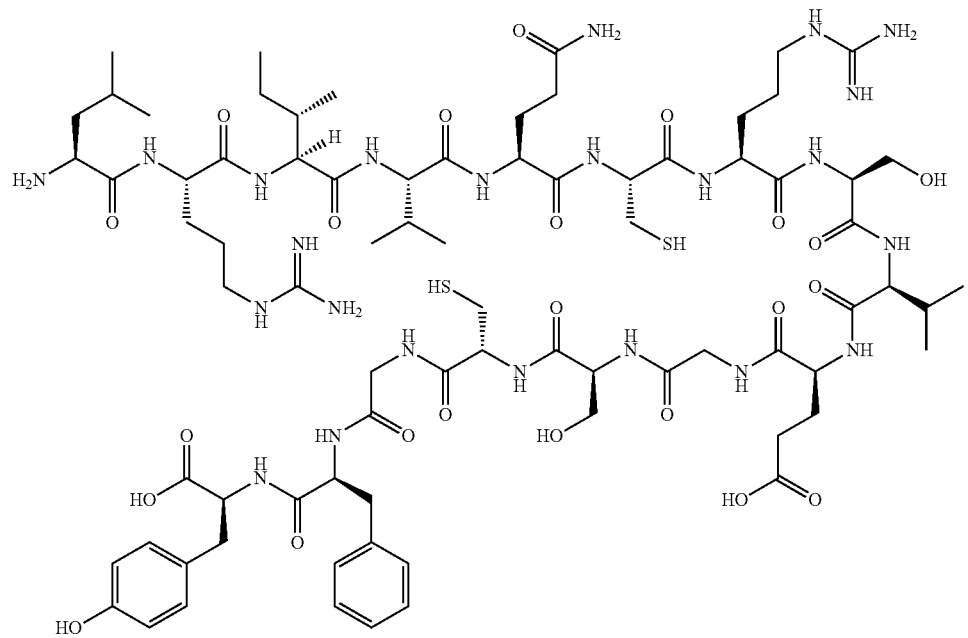
AOD-9604
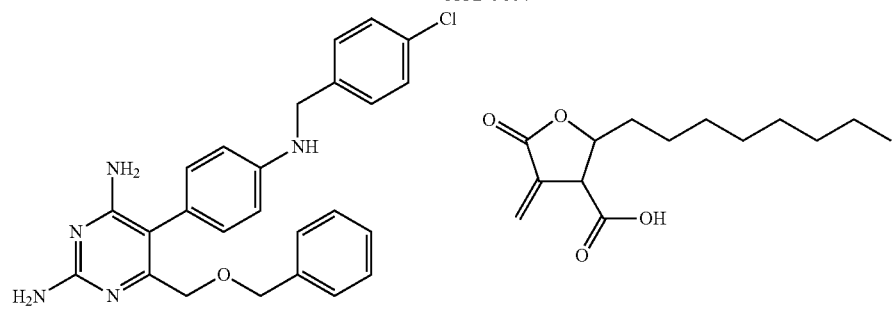
A-778193        C75

-continued
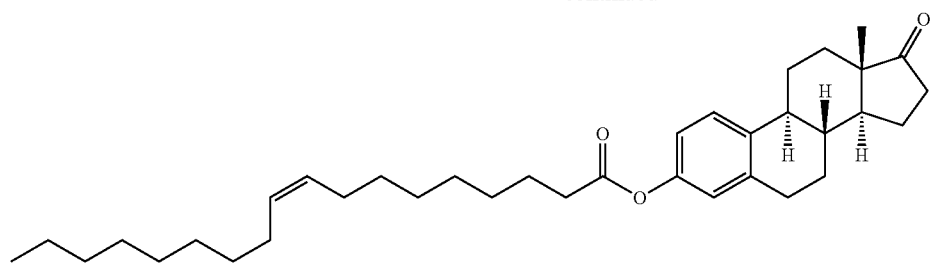
Oleoyl-Estrone
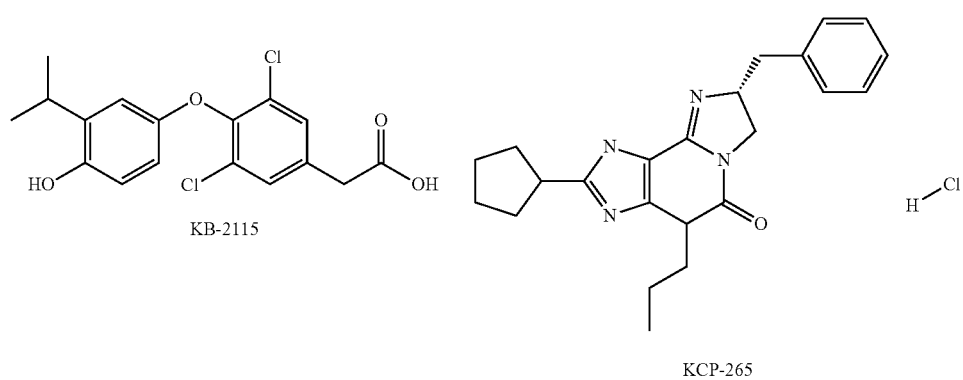
KB-2115
KCP-265
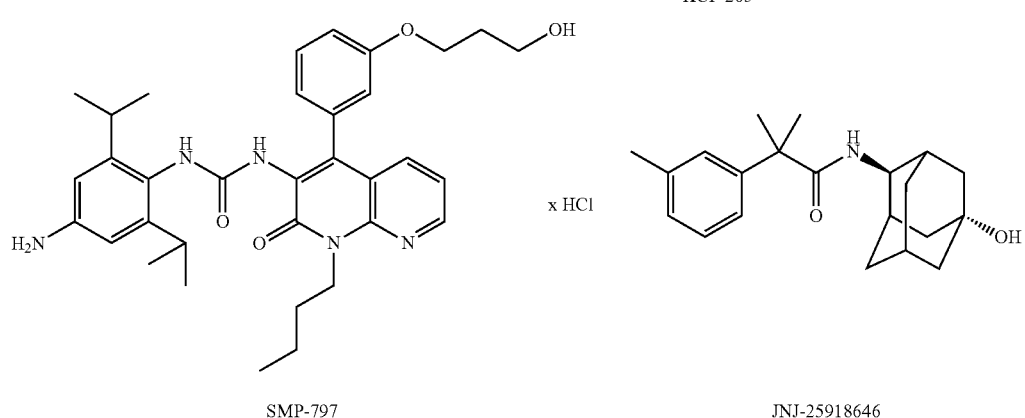
SMP-797
JNJ-25918646
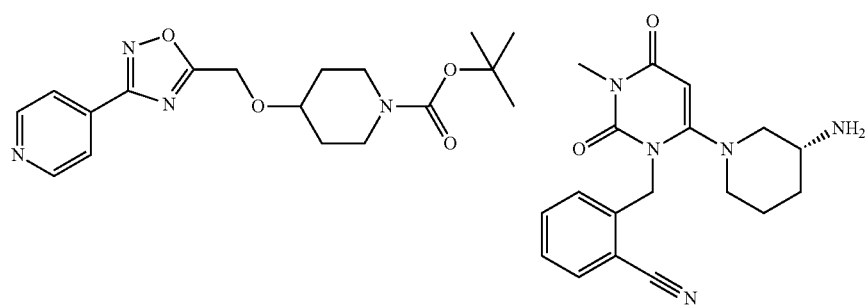
PSN-632408
SYR-322
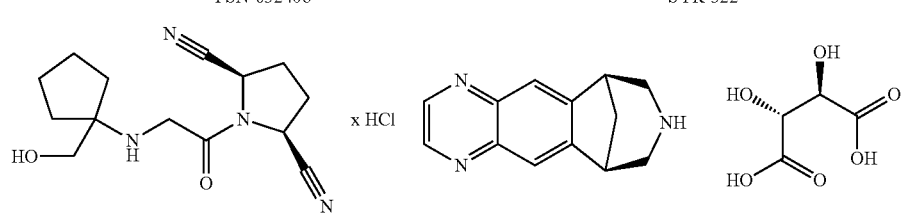
DP-893
Varenicline Tartrate -continued
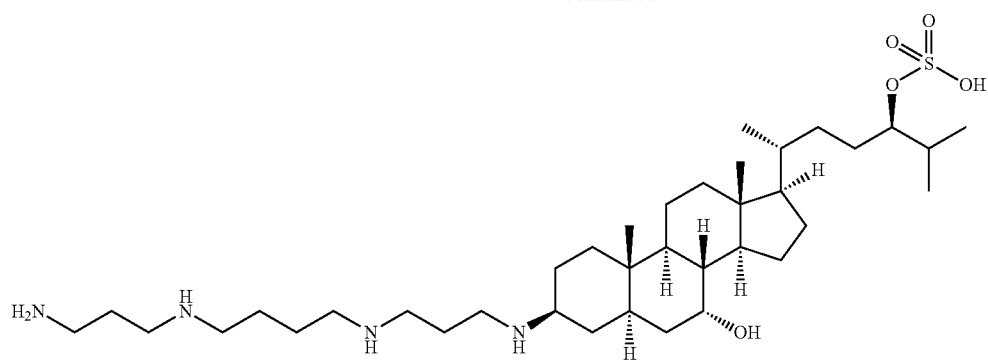
Trodusquemine
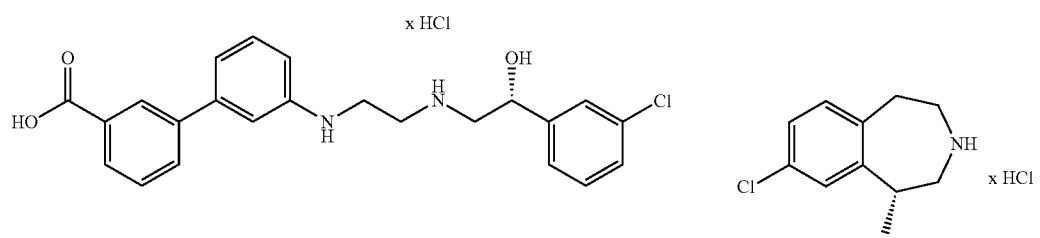
Solabegron
Lorcaserin Hydrochloride
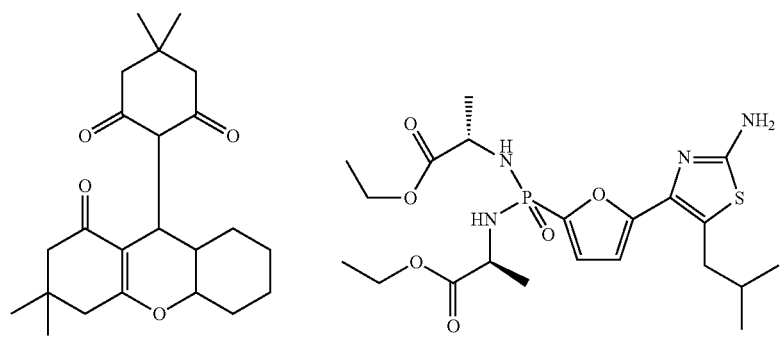
L-152804
MB-06322
CS-917
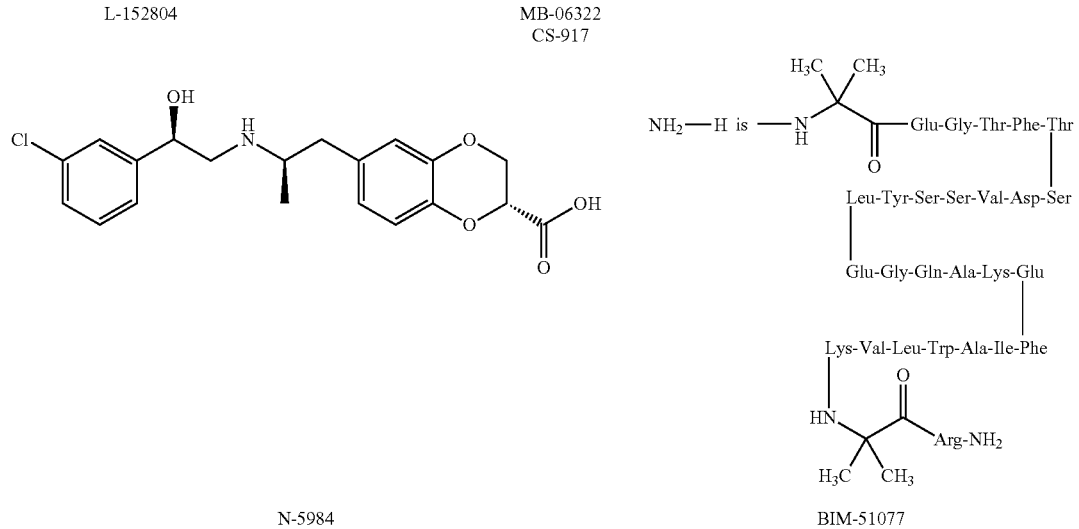
N-5984
BIM-51077

-continued
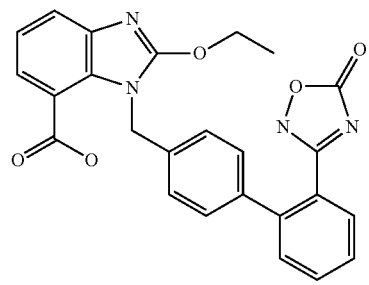
TAK-536
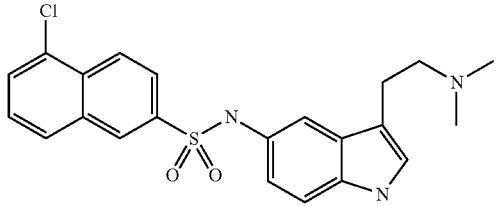
E-6837
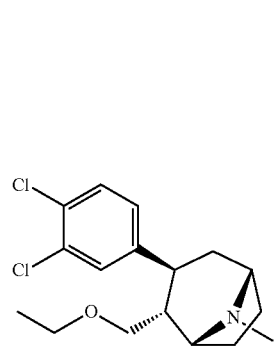
Tesofensine
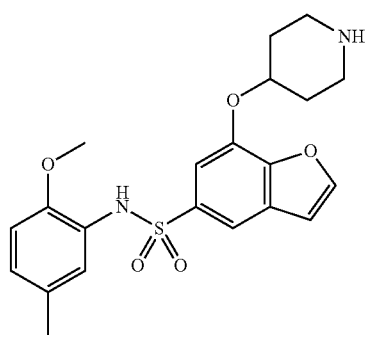
BVT-74316
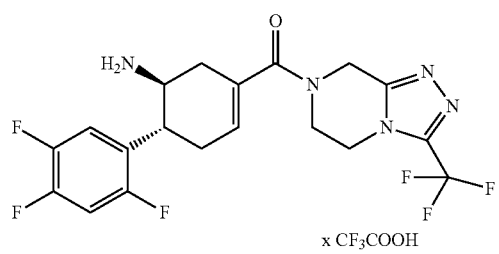
ABT-341
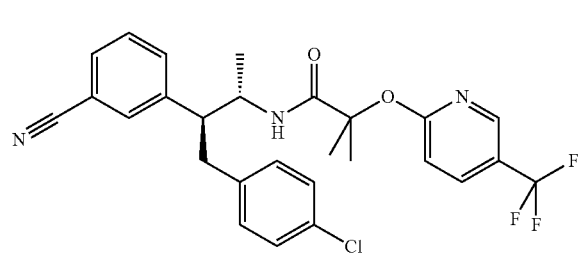
MK-0364
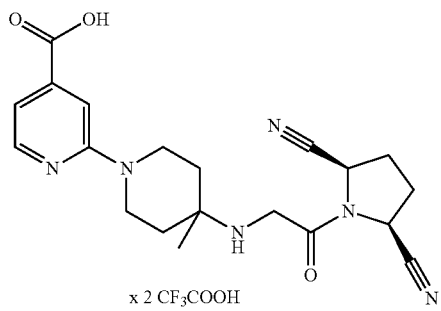
ABT-279
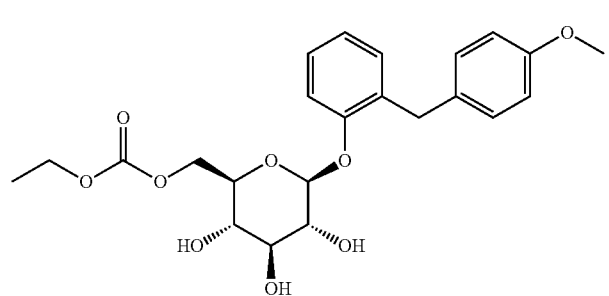
Sergliflozin
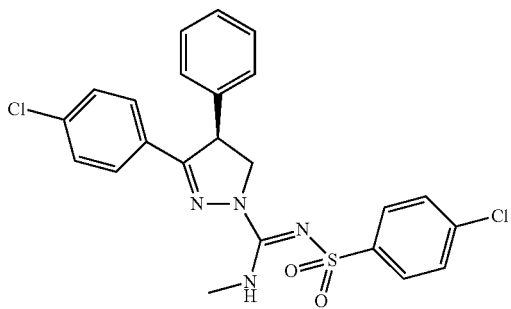
SLV-319

-continued

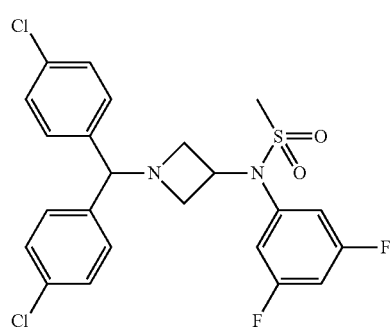
AVE 1625

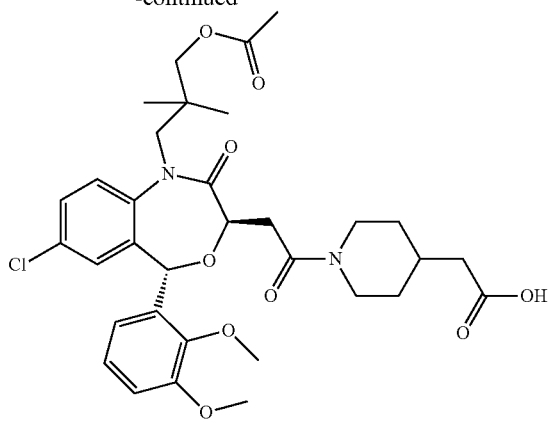
TAK-475

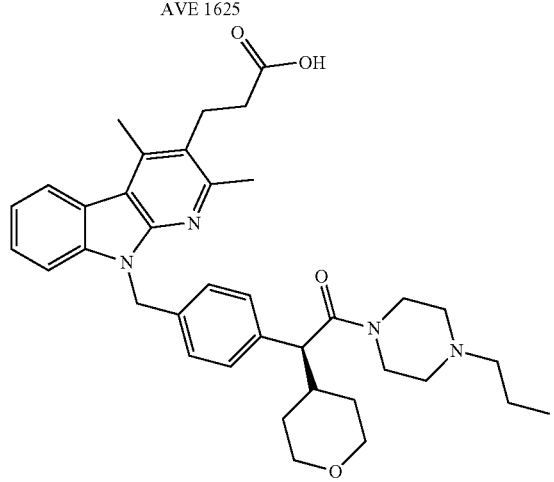
AS-1552133

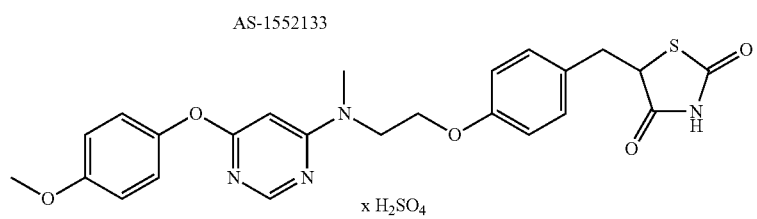
x H₂SO₄

CKD-501 (Lobeglitazone Sulfate)

The activity of the compounds was tested as follows:
Determination of EC50 Values of PPAR Agonists in the Cellular PPARalpha Assay
Principle The potency of substances which bind to human PPARalpha and activate it in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only weak expression of the luciferase reporter gene in the absence of a PPARalpha ligand if fatty acid-depleted fetal calf serum (cs-FCS) is used in the assay. PPARalpha ligands bind and activate the PPARalpha fusion protein and thereby stimulate the expression of the luciferase reporter gene. The luciferase which is formed can be detected by means of chemiluminescence via an appropriate substrate.

Construction of the PPARalpha Reporter Cell Line

The PPARalpha reporter cell line was prepared in two stages. Firstly, the luciferase reporter element was constructed and stably transfected into HEK cells. For this purpose, five binding sites of the yeast transcription factor GAL4 (Accession # AF264724) were cloned in 5"-upstream of a 68 bp-long minimal MMTV promoter (Accession # V01175).

The minimal MMTV promoter section contains a CCAAT box and a TATA element in order to enable efficient transcription by RNA polymerase II. The cloning and sequencing of the GAL4-MMTV construct took place in analogy to the description of Sambrook J. et. al. (Molecular cloning, Cold Spring Harbor Laboratory Press, 1989). Then the complete *Photinus pyralis* gene (Accession # M15077) was cloned in 3'-downstream of the GAL4-MMTV element. After sequencing, the luciferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Accession # P04150) was linked to the cDNA section coding for amino acids 1-147 of the yeast transcription factor GAL4 (Accession # PO4386). The cDNA of the ligand-binding domain of the human PPARalpha receptor (amino acids S167-Y468; Accession # S74349) was cloned in at the 3'-end of this GR-GAL4 construct. The fusion construct prepared in this way (GR-GAL4-humanPPARalpha-LBD) was recloned into the plasmid pcDNA3 (Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARalphareporter cell line is cultivated to 80% confluence in DMEM (#41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% CO2. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% CO2 for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin). Test substances are tested in 11 different concentrations in the range from 10 µM to 100 pM. More potent compounds are tested in concentration ranges from 1 µM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% CO2 for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

Determination of EC50 Values of PPAR Agonists in the Cellular PPARdelta Assay

Principle

The potency of substances which bind to human PPARdelta and activate it in an agonistic manner is analyzed using a stably transfected HEK cell line (HEK=human embryo kidney) which is referred to here as PPARdelta reporter cell line. In analogy to the assay described for PPARalpha, the PPARdelta reporter cell line also contains two genetic elements, a luciferase reporter element (pdeltaM-GAL4-Luc-Zeo) and a PPARdelta fusion protein (GR-GAL4-humanPPARdelta-LBD) which mediates expression of the luciferase reporter element depending on a PPARdelta ligand. The stably and constitutively expressed fusion protein GR-GAL4-humanPPARdelta-LBD binds in the cell nucleus of the PPARdelta reporter cell line via the GAL4 protein portion to the GAL4 DNA binding motifs 5'-upstream of the luciferase reporter element which is stably integrated in the genome of the cell line. There is only little expression of the luciferase reporter gene in the absence of a PPARdelta ligand if fatty acid-depleted fetal calf serum (cs-FCS) is used in the assay. PPARdelta ligands bind and activate the PPARdelta fusion protein and thereby stimulate expression of the luciferase reporter gene. The luciferase which is formed can be detected by means of chemiluminescence via an appropriate substrate.

Construction of the PPARdelta Reporter Cell Line

The production of the stable PPARdelta reporter cell line is based on a stable HEK-cell clone which was stably transfected with a luciferase reporter element. This step was already described above in the section "construction of the PPARalpha reporter cell line". In a second step, the PPARdelta fusion protein (GR-GAL4-humanPPARdelta-LBD was stably introduced into this cell clone. For this purpose, the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARdelta receptor (amino acids S139-Y441; Accession # L07592) was cloned in at the 3'-end of this GR-GAL4 construct. The fusion construct prepared in this way (GR-GAL4-humanPPARdelta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPARdelta reporter cell line which contains a luciferase reporter element and constitutively expresses the PPARdelta fusion protein (GR-GAL4-human PPARdelta-LBD) was isolated by selection with zeocin (0.5 mg/ml) and G418 (0.5 mg/ml).

Assay Procedure and Evaluation

The activity of PPARdelta agonists is determined in a 3-day assay in exact analogy to the procedure already described for the PPARalpha reporter cell line except that the PPARdelta reporter cell line and a specific PPARdelta agonist was used as a standard to control test efficacy.

PPARdelta EC50 values in the range from 1 nM to >10 µM were measured for the PPAR agonists described in this application. Compounds of the invention of the formula I activate the PPARdelta receptor.

Determination of EC50 Values of PPAR Agonists in the Cellular PPARgamma Assay

Principle

A transient transfection system is employed to determine the cellular PPARgamma activity of PPAR agonists. It is based on the use of a luciferase reporter plasmid (pGL3basic-5×GAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARgamma assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5×GAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3'), together with a 160 bp-long thymidine kinase promoter section (Genbank Accession # AF027128) 5'-upstream into pGL3basic. 3'-downstream of the thymidine kinase promoter is the complete luciferase gene from *Photinus pyralis* (Genbank Accession # M15077) which is already a constituent of the plasmid pGL3basic used. The cloning and sequencing of the reporter plasmid pGL3basic-5×GAL4-TK took place in analogy to the description in Sambrook J. et. al. (Molecular cloning, Cold Spring Harbor Laboratory Press, 1989). The PPARgamma expression plasmid pcDNA3-GAL4-humanPPARgammaLBD was prepared by first cloning the cDNA coding for amino acids 1-147 of the yeast transcription factor GAL4 (Genbank Accession # P04386) into the plasmid pcDNA3 (from Invitrogen) 3'-downstream of the cytomegalovirus promoter. Subsequently, the cDNA of the ligand-binding domain (LBD) of the human PPARgamma receptor (amino acids I152-Y475; Accession # g1480099) 3'-downstream of the GAL4 DNA binding domain. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5×GAL4-TK and the PPARgamma expression plasmid pcDNA3-GAL4-humanPPARgammaLBD, also used for the cellular PPARgamma assay are the reference plasmid pRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM (#41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

Firstly, solution A, a transfection mixture which contains all four plasmids previously described in addition to DMEM, is prepared. The following amounts are used to make up 3 ml of solution A for each 96 well microtiter plate for an assay: 2622 µl of antibiotic- and serum-free DMEM (#41965-039, Invitrogen), 100 µl of reference plasmid pRL-CMV (1 ng/µl), 100 µl of luciferase reporter plasmid pGL3basic-5×GAL4-TK (10 ng/µl), 100 µl of PPARgamma expression plasmid pcDNA3-GAL4-humanPPARgammaLBD (100 ng/µl) and 78 µl of plasmid pBluescript SK(+) (500 ng/µl). Then 2 ml of solution B are prepared by mixing 1.9 ml of DMEM (#41965-039, Invitrogen) with 100 µl of PolyFect transfection reagent (from Qiagen) for each 96 well microtiter plate. Subsequently, 3 ml of solution A are mixed with 2 ml of solution B to give 5 ml of solution C, which is thoroughly mixed by multiple pipetting and incubated at room temperature for 10 min.

80%-confluent HEK cells from a cell culture bottle with a capacity of 175 cm2 are washed once with 15 ml of PBS (#14190-094, Invitrogen) and treated with 3 ml of trypsin solution (#25300-054, Invitrogen) at 37° C. for 2 min. The cells are then taken up in 15 ml of DMEM (#41965-039, Invitrogen) which is mixed with 10% FCS (#16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250,000 cells/ml. 15 ml of this cell suspension are mixed with 5 ml of solution C for one microtiter plate. 200 µl of the suspension are seeded in each well of a 96 well microtiter plate with a clear plastic base (#3610, Corning Costar). The plates are incubated in a cell culture incubator at 37° C. and 5% CO2 for 24 h.

Day 2

PPAR agonists to be tested are dissolved in DMSO in a concentration of 10 mM. This stock solution is diluted in DMEM (#41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 µM to 100 pM. More potent compounds are tested in concentration ranges from 1 µM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 µl per well of a 96 well microtiter plate. Each plate is charged with a standard PPARgamma agonist, which is likewise diluted in 11 different concentrations, in order to demonstrate the functioning of the assay in each individual plate. The assay plates are incubated in an incubator at 37° C. and 5% CO2.

Day 4

After removal of the medium by aspiration, 50 µl of Dual-Glo™ reagent (Dual-Glo™ Luciferase Assay System; Promega) are added to each well in accordance with the manufacturer's instructions in order to lyze the cells and provide the substrate for the firefly luciferase (*Photinus pyralis*) formed in the cells. After incubation at room temperature in the dark for 10 minutes, the firefly luciferase-mediated chemiluminescence is measured in a measuring instrument (measuring time/well 1 sec; Trilux from Wallac). Then 50 µl of the Dual-Glo™ Stop & Glo reagent (Dual-Glo™ Luciferase Assay System; Promega) is added to each well in order to stop the activity of the firefly luciferase and provide the substrate for the *Renilla luciferase* expressed by the reference plasmid pRL-CMV. After incubation at room temperature in the dark for a further 10 minutes, a chemiluminescence mediated by the *Renilla luciferase* is again measured for 1 sec/well in the measuring instrument.

Evaluation

The crude data from the luminometer are transferred into a Microsoft Excel file. The firefly/*Renilla luciferase* activity ratio is determined for each measurement derived from one well of the microtiter plate. The dose-effect plots and EC50 values of PPAR agonists are calculated from the ratios by the XL.Fit program as specified by the manufacturer (IDBS).

PPARgamma EC50 values in the range from 1 nM to >10 µM were measured for the PPAR agonists described in this application. Compounds of the invention of the formula I activate the PPARgamma receptor.

The examples given in Table I serve to illustrate the invention, but without limiting it.

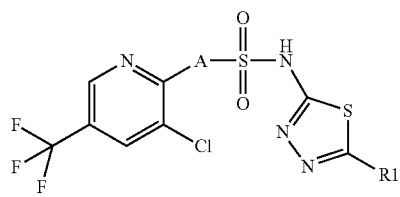

I

TABLE I

The dotted line indicates the connection of the sulfonamide group.

| Example | R1 | A |
|---|---|---|
| 1 | —CH(CH3)2 | 1-(4-substituted-phenyl)cyclohexyl-CH2-N (azaspiro) |
| 2 | —CH(CH3)2 | 2-(4-substituted-phenyl)cyclopentyl-1-N |
| 3 | —CH(CH3)2 | 2-(4-substituted-phenyl)cyclopentyl-1-N (stereoisomer) |
| 4 | —CH(CH3)2 | 1-(4-substituted-phenyl)cyclopentyl-CH2-N |
| 5 | —CH(CH3)2 | 2-aminoindan-5-yl |
| 6 | —CF3 | 1-(4-substituted-phenyl)cyclopentyl-CH2-N |
| 7 | —CF3 | 2-(4-substituted-phenyl)cyclopentyl-1-N |
| 8 | —CH(CH3)2 | 6-chloro-2-aminoindan-5-yl |
| 9 | —CF3 | 2-aminoindan-5-yl |
| 10 | —CH(CH3)2 | 6-methoxy-2-aminoindan-5-yl |
| 11 | —C6H5 | 2-aminoindan-5-yl |

TABLE I-continued

The dotted line indicates the connection of the sulfonamide group.

| Example | R1 | A |
|---|---|---|
| 12 | —Cyclohexyl | |
| 13 | —Cyclopropyl | |
| 14 | —CH(CH3)2 | |
| 15 | —CH(CH3)2 | |
| 16 | —CH(CH3)2 | |
| 17 | —CH(CH3)2 | |

The potency of some of the described examples are indicated in the following table:

| Example | PPARdelta EC50 (µM) | PPARgamma EC50 (µM) |
|---|---|---|
| 1 | 0.06 | 0.026 |
| 2 | 0.067 | 0.647 |
| 3 | 0.001 | 1.80 |
| 4 | 0.22 | 0.99 |
| 8 | 0.779 | >10 |

Processes

The compounds of the general formula 1, where R1, R3, R4, R5, R6, and R7 are as defined above, according to the invention can be obtained as outlined to the reaction schemes below:

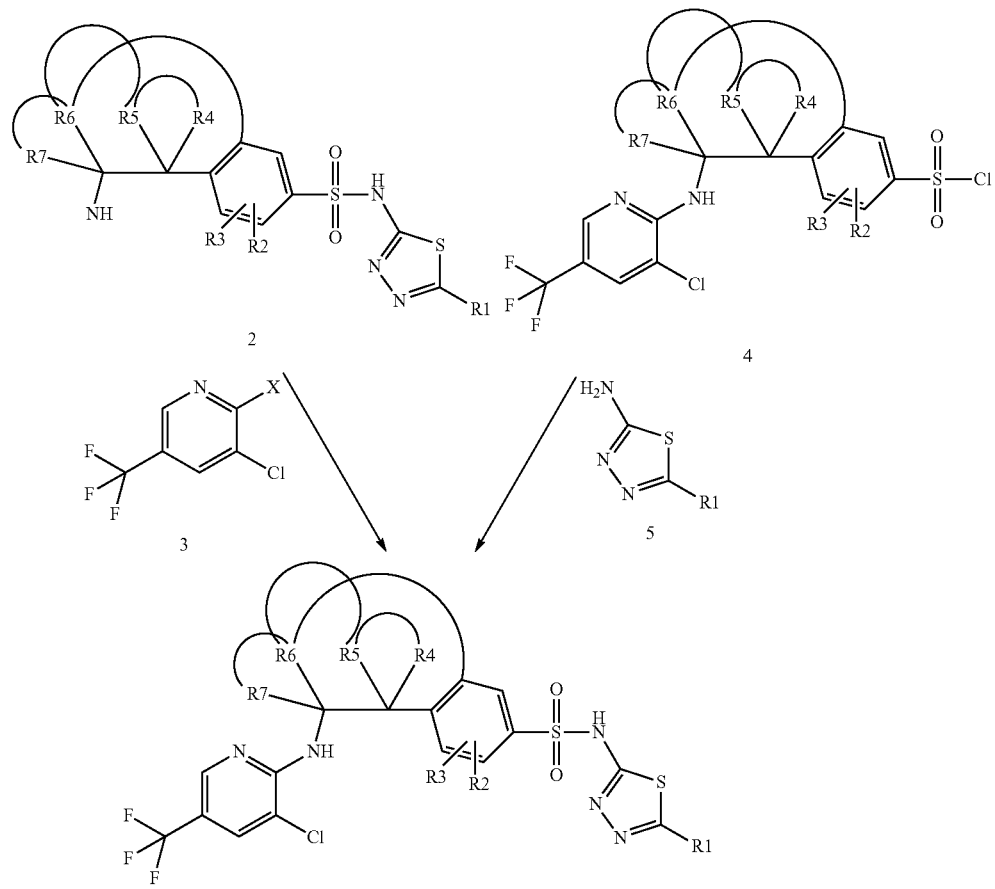

An amine of the general formula 2 is reacted with a compound of the formula 3, where X represents a halogen like F, Cl, Br, I, or an other leaving group, in an appropriate inert solvent at room temperature or at elevated temperature and in the presence of a base like triethylamine or potassium carbonate to afford the compound of the general formula 1.

Alternatively a sulphonylchloride of the general formula 4 is reacted with an amine of the general formula 5 in the presence of a base like triethylamine or pyridine and an inert solvent in the well known manner to yield the desired products of the formula 1. The intermediates 2 and 4 were prepared according to the following scheme:

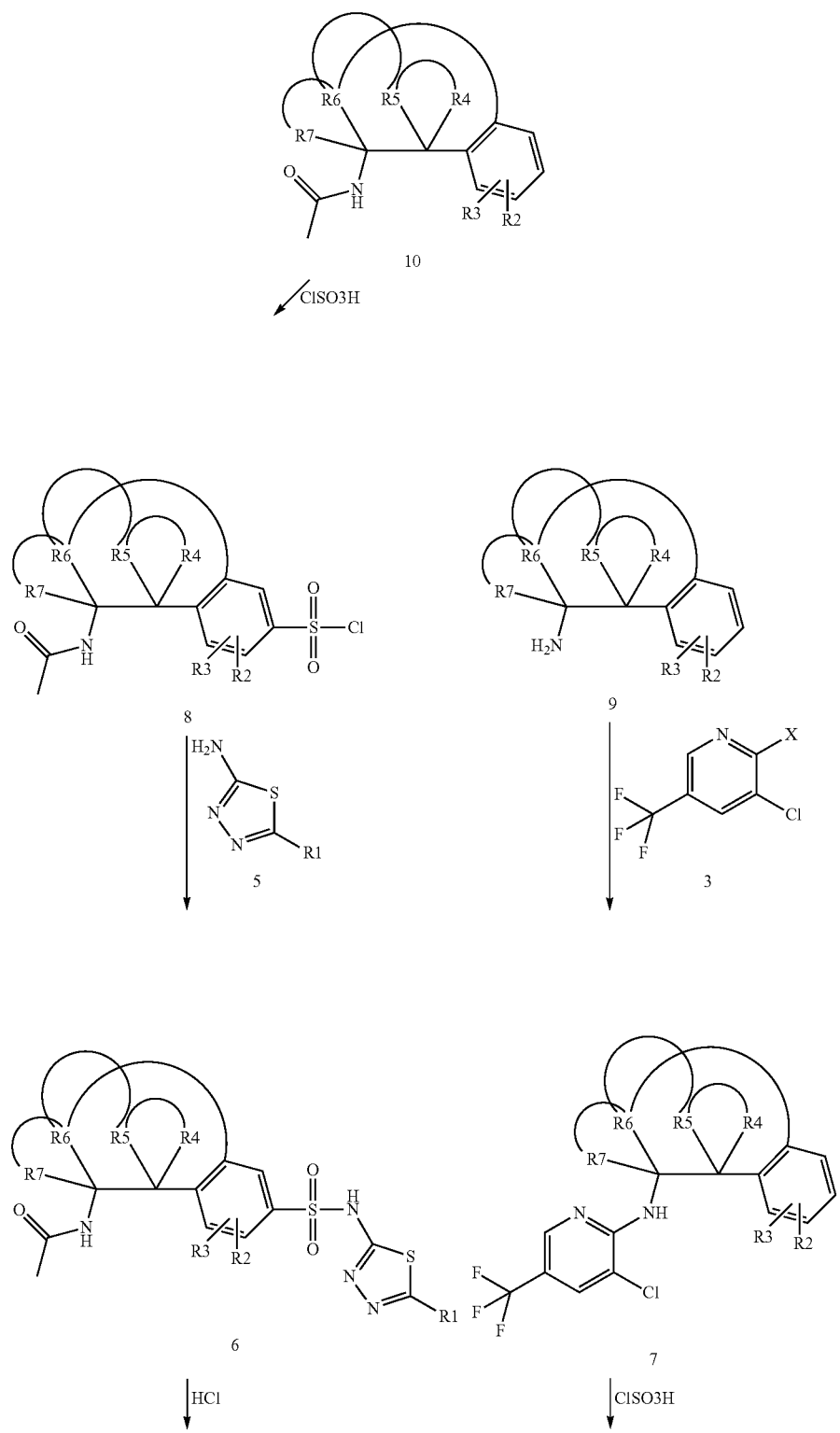

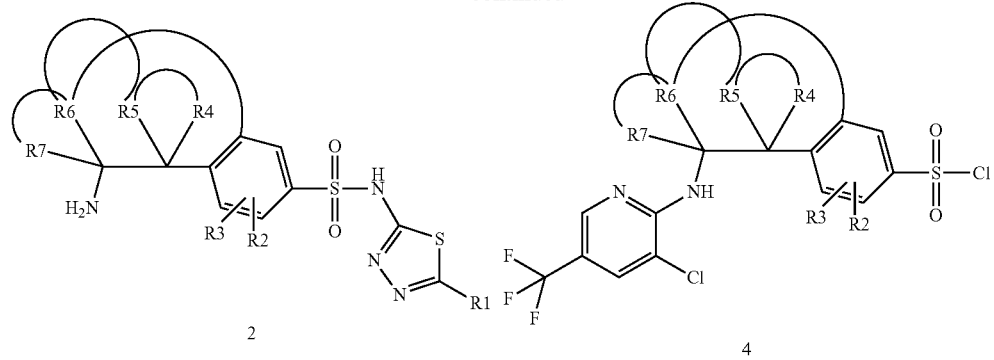

An acetamide of the general formula 10 was reacted with chloro sulfonic acid to give the chlorosulfonyl derivative of the general formula 8, which, on reaction with the amine 5 gives the intermediate 6, that was treated with hydrochloric acid at elevated temperature to the intermediate of the general formula 2.

The intermediate of the general formula 4 was synthesized starting from the amine 9 and the pyridine derivative 3 by heating the reactants in an appropriate solvent at 50 to 150° C. for several hours in the presence of a base, followed by the action of chloro sulfonic acid on the intermediate of the general structure 7.

Other compounds can be obtained accordingly or by known processes.

List of Abbreviation:

| | |
|---|---|
| Ac | acetyl |
| AIBN | 2,2'-azobis(2-methylpropionitrile) |
| Bn | benzyl |
| BOC | tert-butyl-oxy-carbonyl |
| iBu | isobutyl |
| tBu | tert-butyl |
| BuLi | n-butyllithium |
| Bz | benzoyl |
| Cy | cyclohexyl |
| DBU | 1,8-diazabicyclo[5.4.0]undec-7-ene |
| DCI | direct chemical ionization (MS) |
| DCM | dichloromethane |
| DMAP | N,N-dimethylaminopyridine |
| DMF | N,N-dimethylformamide |
| DMSO | dimethylsulfoxide |
| EE | ethyl acetate |
| eq | equivalents |
| ESI | electronspray-Ionisation (MS) |
| FG | leaving group |
| GC | gas chromatography |
| Hal | halogen |
| HPLC | high performance liquid chromatography |
| LC-MS | liquid chromatography coupled with mass-spectroscopy |
| Me | methyl |
| MeCN | acetonitrile |
| MS | mass-spectroscopy |
| MS 4A | molecular sieves four angstrom |
| MsCl | methansulfonylchloride |
| MW | micro wave |
| NBS | N-bromosuccinimide |
| NMR | nuclear magnetic resonance |
| p | para |
| Pd/C | palladium on carbon |
| iPr | isopropyl |
| nPr | n-propyl |
| Rf | retention factor (TLC) |
| tert | tertiary |
| TFA | trifluoroacetic acid |
| THF | tetrahydrofuran |
| TLC | thin layer chromatography |
| TOTU | O-((ethoxycatbonyl)cyanomethyleneamino)-N,N,N',N'-tetramethyluronium-tetrafluoroborat |

Further compounds of the formula I can be prepared correspondingly or by known processes.

The experimental procedures for preparing the examples mentioned above are described below:

EXAMPLE 1

4-{1-[(3-Chloro-5-trifluoromethyl-pyridin-2-ylamino)-methyl]-cyclohexyl}-N-(5-isopropyl-[1,3,4]thiadiazol-2-yl)-benzenesulfonamide

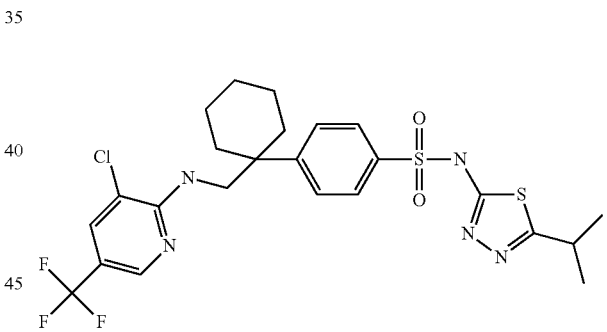

1a) (3-Chloro-5-trifluoromethyl-pyridin-2-yl)-(1-phenyl-cyclohexylmethyl)-amine

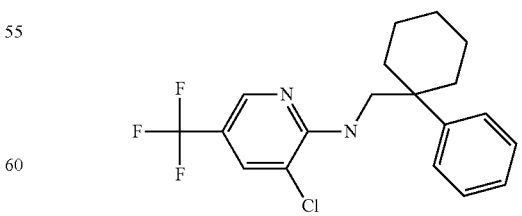

was prepared from 475 mg of 1-phenyl-cyclohexyl-methylamine by reaction with 596 mg of 2,3-dichloro-5-trifluoromethyl-pyridine in the presence of 354 mg potassium carbonate in 2.5 ml of NMP at 80° C. for 1 hour. After dilution with 20 ml of water, the product was extracted with 30 ml of ethyl acetate and purified by chromatography on silica gel with the eluents dichloromethane:methanol=98:2 to obtain 469 mg g of a light yellow oil.

MS(ESI): 369 (M+H+)

1b) 4-{1-[(3-Chloro-5-trifluoromethyl-pyridin-2-ylamino)-methyl]-cyclohexyl}-benzenesulfonyl chloride

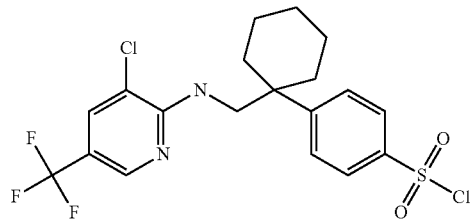 [SMILES: O=S(=O)(Cl)c1ccc(C2(CNc3ncc(C(F)(F)F)cc3Cl)CCCCC2)cc1]

185 mg of (3-Chloro-5-trifluoromethyl-pyridin-2-yl)-(1-phenyl-cyclohexylmethyl)-amine were dissolved in 15 ml of methylenchloride and 0.14 ml of chlorosulfonic acid were added. The reaction mixture was stirred at room temperature for 4 days and than poured on ice water (20 ml). The organic layer was separated, washed twice with 50 ml of brine and then dried over MgSO4. The solvent was removed in vacuo to obtain 194 mg g of the crude product.

MS(ESI): 468 (M+H+).

4-{1-[(3-Chloro-5-trifluoromethyl-pyridin-2-ylamino)-methyl]-cyclohexyl}-N-(5-isopropyl-[1,3,4]thiadiazol-2-yl)-benzenesulfonamide 58 mg of 5-isopropyl-1,2,3-thiadiazol-2-ylamine and 190 mg of 4-{1-[(3-Chloro-5-trifluoromethyl-pyridin-2-ylamino)-methyl]-cyclohexyl}-benzenesulfonyl chloride were dissolved in 2 ml of pyridine and stirred at room temperature overnight. After evaporation of the solvent the residue was purified by chromatography on silica gel with the eluents dichloromethane:methanol=9:1 to obtain 50 mg of the product.

MS(ESI): 575 (M+H+)

EXAMPLE 2

Trans-4-[(1S,2R)-2-(3-chloro-5-trifluoromethyl-pyridin-2-ylamino)-cyclopentyl]-N-(5-isopropyl-[1,3,4]thiadiazol-2-yl)-benzene-sulfonamide

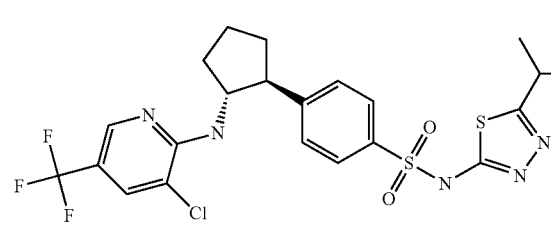

EXAMPLE 2a

N-(2-Phenyl-cyclopentyl)-acetamide

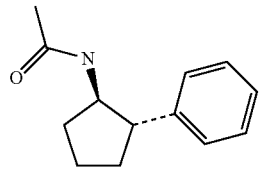

MS(ESI): 204 (M+H+)

4.45 g of trans-2-phenyl-cyclopentylamine and 4.2 ml of triethylamine were dissolved in 50 ml of ethyl acetate. 2.86 ml of acetic anhydride was added slowly and the mixture stirred for 1 hour and washed with 40 ml of water. After drying the organic layer with sodium sulfate, filtration and evaporation 4.7 g of a crude solid was obtained that was used without further purification.

EXAMPLE 2b

Trans-4-(2-acetylamino-cyclopentyl)-benzenesulfonyl chloride

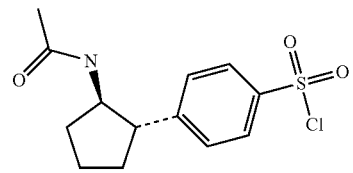 [SMILES: CC(=O)N[C@@H]1CCC[C@H]1c1ccc(S(=O)(=O)Cl)cc1]

MS(ESI): 302 (M+H+)

4.7 g of the crude product of example 2a were dissolved in 90 ml of dichloromethane. To this mixture 5.4 ml of chloro sulfonic acid were added drop by drop under stirring at room temperature. The reaction mixture was heated at 50° C. for 1 hour and, after cooling to room temperature, triturated with 70 ml of ice water. After separating the organic layer was dried over sodium sulfate and evaporated to dryness yielding 4.4 g of the crude product.

EXAMPLE 2c

Trans-N-{2-[4-(5-isopropyl-[1,3,4]thiadiazol-2-yl-sulfamoyl)-phenyl]-cyclopentyl}-acetamide

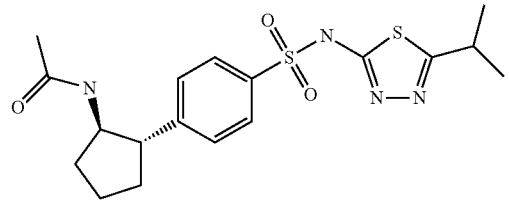 [SMILES: CC(=O)N[C@@H]1CCC[C@H]1c1ccc(S(=O)(=O)Nc2nnc(C(C)C)s2)cc1]

608 mg of trans-4-(2-acetylamino-cyclopentyl)-benzene-sulfonyl chloride, 3 ml of pyridine and 286 mg of 5-Isopropyl-1,3,4-thiadiazol-2-ylamine were stirred at room temperature for 30 minutes. The solvent was evaporated, the residue was treated with 20 ml 2n hydrochloric acid and the product extracted with 30 ml ethyl acetate and purified by column chromatography (silca gel, DCM:methanol=96:4).

Yield: 150 mg MS(ESI): 409 (M+H+)

EXAMPLE 2d

Trans-4-(2-amino-cyclopentyl)-N-(5-isopropyl-[1,3,4]thiadiazol-2-yl)-benzenesulfonamide hydrochloride

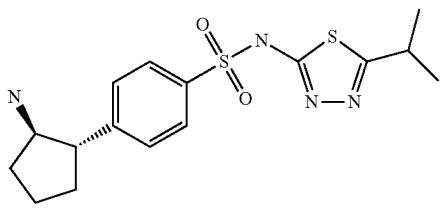 [SMILES: CC(C)c1nnc(NS(=O)(=O)c2ccc([C@@H]3CCC[C@H]3N)cc2)s1]

Was prepared from 150 mg trans-N-{2-[4-(5-isopropyl-[1,3,4]thiadiazol-2-ylsulfamoyl)-phenyl]-cyclopentyl}-acetamide by heating it in 10 ml of 2n HCl at 100° C. for 13 hours.

Yield: 135 mg MS(ESI): 367 (M+H+)

Trans-4-[(1S,2R)-2-(3-chloro-5-trifluoromethyl-pyridin-2-ylamino)-cyclopentyl]-N-(5-isopropyl-[1,3,4]thiadiazol-2-yl)benzene-sulfonamide

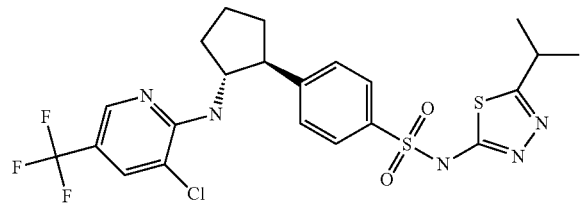 [SMILES: CC(C)c1nnc(NS(=O)(=O)c2ccc([C@@H]3CCC[C@H]3Nc3ncc(C(F)(F)F)cc3Cl)cc2)s1]

MS(ESI): 547 (M+H+)

The mixture of 29 mg of 2,3-dichloro-5-trifluoromethyl-pyridin, 28 mg of potassium carbonate, 1.5 ml NMP and 53 mg trans-4-(2-amino-cyclopentyl)-N-(5-isopropyl-[1,3,4]thiadiazol-2-yl)-benzenesulfonamide hydrochloride was stirred at 105° C. for 10 hours. After diluting it with 10 ml of water the product was extracted with 20 ml of ethyl acetate and purified by chromatography on silica gel with the eluents dichloromethane:methanol=98:2 to obtain 19.5 mg of the product.

MS(ESI): 547 (M+H+)

EXAMPLE 3

Cis-4-[(1S,2R)-2-(3-chloro-5-trifluoromethyl-pyridin-2-ylamino)-cyclopentyl]-N-(5-isopropyl-[1,3,4]thiadiazol-2-yl)-benzene-sulfonamide

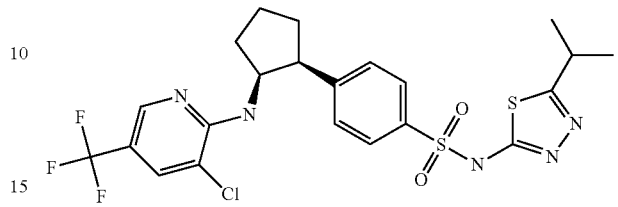

MS(ESI): 547 (M+H+)
was prepared by a procedure similar to the preparation described in example 2 starting from cis-2-phenyl-cyclopentylamine

EXAMPLE 4

4-{1-[(3-Chloro-5-trifluoromethyl-pyridin-2-ylamino)-methyl]-cyclopentyl}-N-(5-isopropyl-[1,3,4]thiadiazol-2-yl)-benzene-sulfonamide

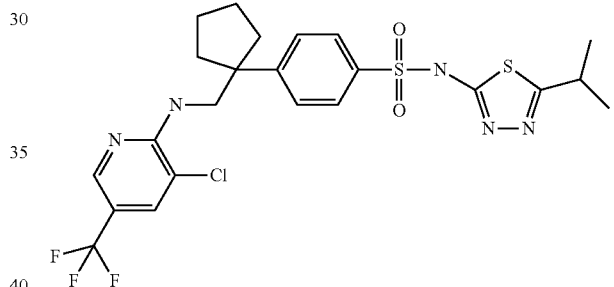

MS(ESI): 561 (M+H+)
was prepared by a procedure similar to the preparation described in example 2 starting from (1-phenyl-cyclopentyl)-methylamine.

EXAMPLE 5

2-(3-Chloro-5-trifluoromethyl-pyridin-2-ylamino)-indan-5-sulfonic acid (5-isopropyl-[1,3,4]thiadiazol-2-yl)amide

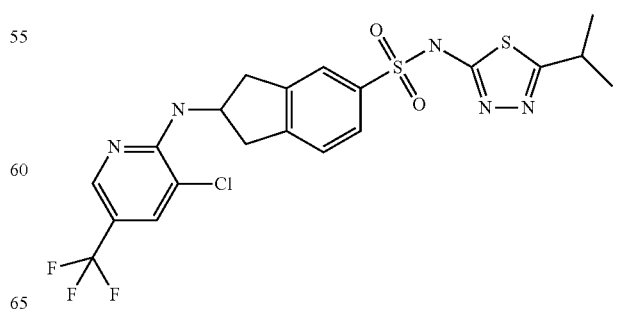

MS(ESI): 518 (M+H+)

was prepared by a procedure similar to the preparation described in example 2 starting from indan-2-ylamine.

EXAMPLE 6

4-{1-[(3-Chloro-5-trifluoromethyl-pyridin-2-ylamino)-methyl]-cyclopentyl}-N-(5-trifluoromethyl-[1,3,4]thiadiazol-2-yl)-benzenesulfonamide

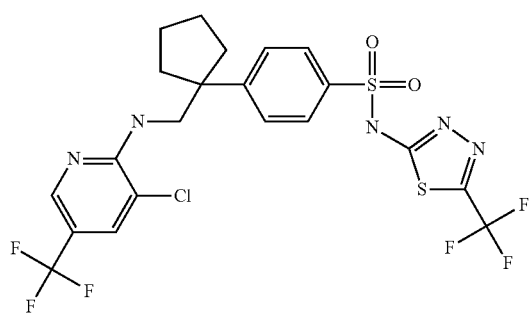 [SMILES: O=S(=O)(Nc1nnc(C(F)(F)F)s1)c1ccc(C2(CNc3ncc(C(F)(F)F)cc3Cl)CCCC2)cc1]

MS(ESI): 586 (M+H+)

was prepared by a procedure similar to the preparation described in example 2 starting from 1-phenylcyclopentyl-methylamine.

EXAMPLE 7

3 4-[(1S,2R)-2-(3-Chloro-5-trifluoromethyl-pyridin-2-ylamino)-cyclopentyl]-N-(5-trifluoromethyl-[1,3,4]thiadiazol-2-yl)-benzene-sulfonamide

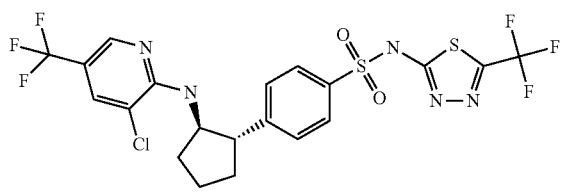 [SMILES: O=S(=O)(Nc1nnc(C(F)(F)F)s1)c1ccc([C@@H]2CCC[C@H]2Nc2ncc(C(F)(F)F)cc2Cl)cc1]

MS(ESI): 572 (M+H+)

was prepared by a procedure similar to the preparation described in example 1 starting from trans-2-phenyl-cyclopentylamine.

EXAMPLE 8

6-Chloro-2-(3-chloro-5-trifluoromethyl-pyridin-2-ylamino)-indan-5-sulfonic acid (5-isopropyl-[1,3,4]thiadiazol-2-yl)amide

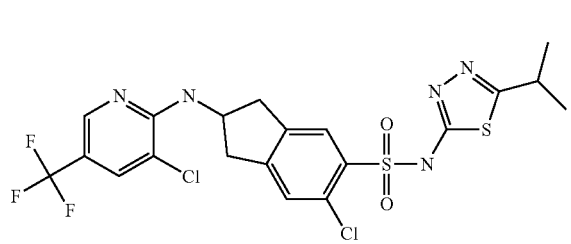 [SMILES: CC(C)c1nnc(NS(=O)(=O)c2cc3c(cc2Cl)CC(Nc2ncc(C(F)(F)F)cc2Cl)C3)s1]

MS(ESI): 553 (M+H+)

was prepared by a procedure similar to the preparation described in example 2 starting from 5-chloro-indan-2-ylamine.

EXAMPLE 9

2-(3-Chloro-5-trifluoromethyl-pyridin-2-ylamino)-indan-5-sulfonic acid (5-trifluoromethyl-[1,3,4]thiadiazol-2-yl)amide

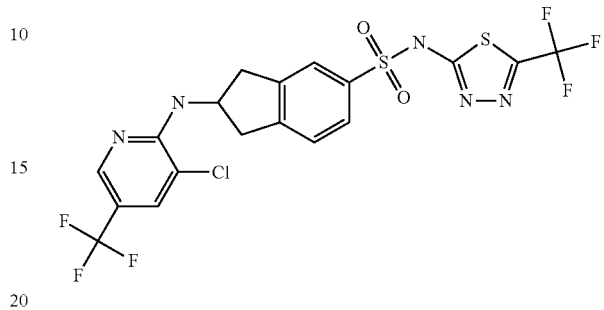

MS(ESI): 544 (M+H+)

was prepared by a procedure similar to the preparation described in example 2 starting from indan-2-ylamine and 2-amino-5-trifluoromethyl-1,3,4-thiadiazole.

EXAMPLE 10

2-(3-Chloro-5-trifluoromethyl-pyridin-2-ylamino)-6-methoxy-indan-5-sulfonic acid (5-isopropyl-[1,3,4]thiadiazol-2-yl)-amide

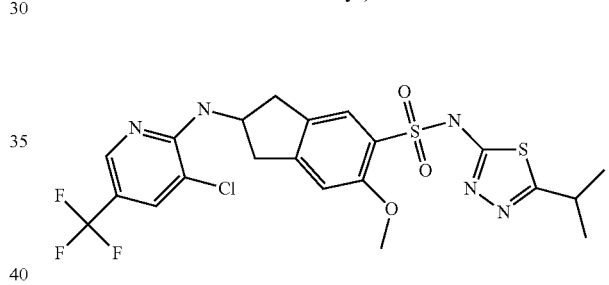

MS(ESI): 549 (M+H+)

was prepared by a procedure similar to the preparation described in example 2 starting from 5-methoxy-indan-2-ylamine and 2-amino-5-isopropyl-1,3,4-thiadiazole.

EXAMPLE 11

2-(3-Chloro-5-trifluoromethyl-pyridin-2-ylamino)-indan-5-sulfonic acid (5-phenyl-[1,3,4]thiadiazol-2-yl)amide

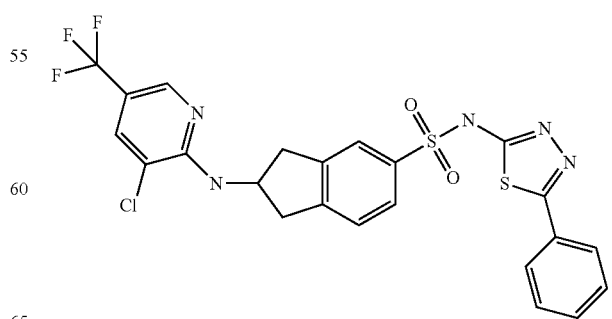

MS(ESI): 553 (M+H+)

was prepared by a procedure similar to the preparation described in example 2 starting from indan-2-ylamine and 2-amino-5-phenyl-1,3,4-thiadiazole.

EXAMPLE 12

2-(3-Chloro-5-trifluoromethyl-pyridin-2-ylamino)-indan-5-sulfonic acid (5-cyclohexyl-[1,3,4]thiadiazol-2-yl)-amide

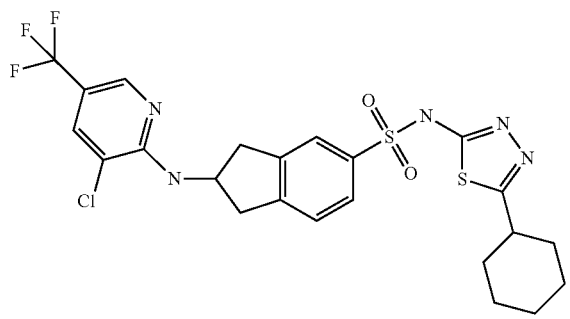 [SMILES: O=S(=O)(Nc1nnc(C2CCCCC2)s1)c1ccc2c(c1)CC(Nc1ncc(C(F)(F)F)cc1Cl)C2]

MS(ESI): 559 (M+H+)

was prepared by a procedure similar to the preparation described in example 2 starting from indan-2-ylamine and 2-amino-5-cyclohexyl-1,3,4-thiadiazole.

EXAMPLE 13

2-(3-Chloro-5-trifluoromethyl-pyridin-2-ylamino)-indan-5-sulfonic acid (5-cyclopropyl-[1,3,4]thiadiazol-2-yl)-amide

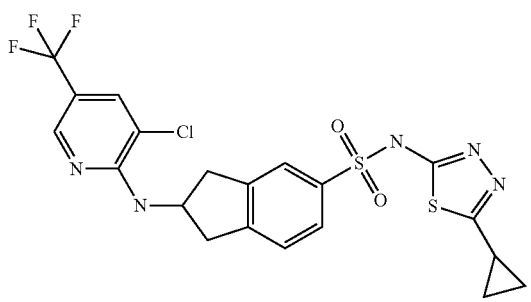 [SMILES: O=S(=O)(Nc1nnc(C2CC2)s1)c1ccc2c(c1)CC(Nc1ncc(C(F)(F)F)cc1Cl)C2]

MS(ESI): 517 (M+H+)
was prepared by a procedure similar to the preparation described in example 2 starting from indan-2-ylamine and 2-amino-5-cyclopropyl-1,3,4-thiadiazole.

EXAMPLE 14

2-(3-Chloro-5-trifluoromethyl-pyridin-2-ylamino)-3-methyl-indan-5-sulfonic acid (5-isopropyl-[1,3,4]thiadiazol-2-yl)amide

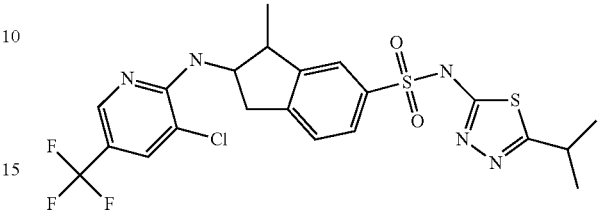

MS(ESI): 533 (M+H+)
was prepared by a procedure similar to the preparation described in example 2 starting from 1-methyl-indan-2-ylamine and 2-amino-5-isopropyl-1,3,4-thiadiazole.

EXAMPLE 15

2-(3-Chloro-5-trifluoromethyl-pyridin-2-ylamino)-6-methyl-indan-5-sulfonic acid (5-isopropyl-[1,3,4]thiadiazol-2-yl)amide

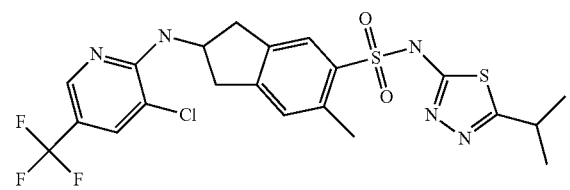 [SMILES: Cc1cc2c(cc1S(=O)(=O)Nc1nnc(C(C)C)s1)CC(Nc1ncc(C(F)(F)F)cc1Cl)C2]

MS(ESI): 533 (M+H+)
was prepared by a procedure similar to the preparation described in example 2 starting from 5-methyl-indan-2-ylamine and 2-amino-5-isopropyl-1,3,4-thiadiazole.

EXAMPLE 16

4-{1-[(3-Chloro-5-trifluoromethyl-pyridin-2-ylamino)-methyl]-cyclobutyl}-N-(5-isopropyl-[1,3,4]thiadiazol-2-yl)-benzenesulfonamide

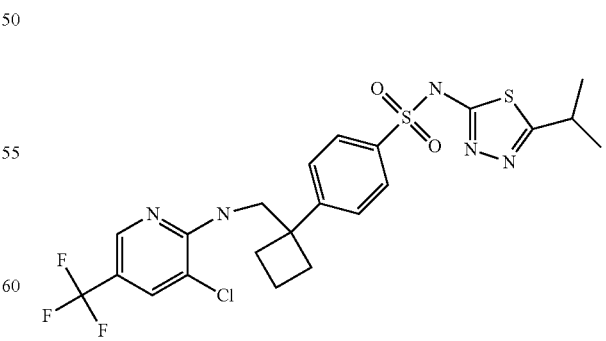

MS(ESI): 547 (M+H+)
was prepared by a procedure similar to the preparation described in example 2 starting from (1-Phenyl-cyclobutyl)-methylamine and 2-amino-5-isopropyl-1,3,4-thiadiazole.

EXAMPLE 17

2-(3-Chloro-5-trifluoromethyl-pyridin-2-ylamino)-6-(2,2,2-trifluoro-ethoxy)-indan-5-sulfonic acid (5-isopropyl-[1,3,4]thiadiazol-2-yl)amide

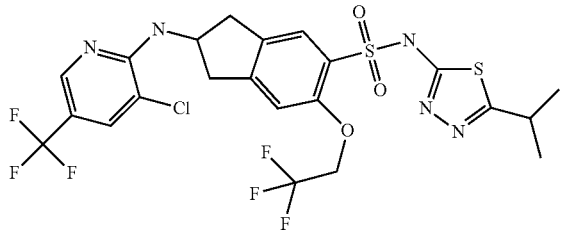 [SMILES: CC(C)c1nnc(NS(=O)(=O)c2cc3c(cc2OCC(F)(F)F)CC(Nc2ncc(C(F)(F)F)cc2Cl)C3)s1]

MS(ESI): 617 (M+H+)
was prepared by a procedure similar to the preparation described in example 2 starting from 5-(2,2,2-trifluoro-ethoxy)-indan-2-ylamine and 2-amino-5-isopropyl-1,3,4-thiadiazole.

---

---

We claim:

1. A compound of formula I:

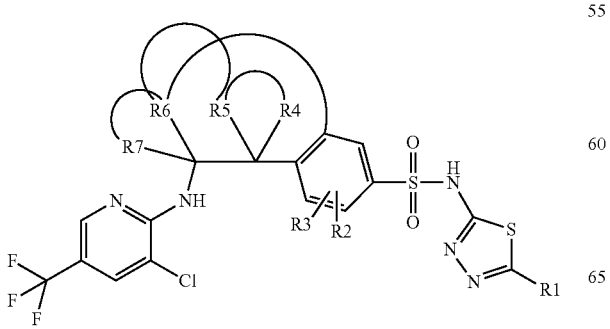

wherein

R1 is (C1-C6) alkyl, (C0-C6) alkylene(C3-C6) cycloalkyl, (C0-C6) alkylene-O-(C1-C6) alkyl, (C0-C6) alkylene-O-(C3-C6) cycloalkyl, (C0-C6) alkylene-(C6-C14)aryl, or (C0-C6) alkylene-(C5-C15) heteroaryl, wherein the alkyl, alkylene, aryl, heteroaryl and cycloalkyl are unsubstituted or mono-, di- or tri-substituted by F, Cl, Br, (C1-C6) alkyl, O—(C1-C6) alkyl, $CF_3$, $OCF_3$, CN, CO—(C1-C6) alkyl, COO(C1-C6) alkyl, CON((C0-C6) alkylene-H)(C0-C6) alkylene-H), or $S(O)_m$(C1-C6) akyl;

R2 and R3 are independently H, halogen, (C1-C6) alkyl, (C0-C4) alkylene-O-(C0-C4) alkylene-H, CN, COO (C1-C6) alkyl, CON((C0-C6) alkylene-H)((C0-C6) alkylene-H), or $S(O)_m$(C1-C6) alkyl, wherein the alkyl and alkylene are unsubstituted or mono-, di- or tri-substituted by F; and R4, R5, R6 and R7 are independently H, (C1-C6) alkyl, (C0-C6) alkylene-(C3-C6) cycloalkyl, (C0-C6) alkylene-(C6-C14)aryl, (C0-C6) alkylene-(C5-C15) heteroaryl, (C0-C6) alkylene-(C3-C15) heterocycloalkyl, or (C0-C6) alkylene-(C3-C15) heterocycloalkenyl, wherein the alkyl, alkylene and cycloalkyl are unsubstituted or mono-, di- or tri-substituted by halogen, (C1-C6) alkyl, (C0-C6) alkylene-O-(C0-C6)-alkylene-H, $CF_3$, $OCF_3$, CN, CO-(C1-C6) alkyl, COO-(C1-C6) alkyl, CON((C0-C6) alkylene-H)((C0-C6) alkylene-H), or $S(O)_m$(C1-C6) alkyl, and wherein the aryl, cycloalkyl, heterocycloalkyl, heterocycloalkenyl and heteroaryl are unsubstituted or mono-, di- or tri-substituted by halogen, CF3, (C1-C6) alkyl or (C0-C4) alkylene-O-(C0-C4) alkylene-H, and wherein at least one pair of R4 and R5, R6 and R7, R5 and R6, together with the C-atoms to which they are connected, or R6 together with the ortho C-atom of the aromatic ring, form a (C3-C9) cycloalkyl, a (C3-C9)-heterocycloalkyl or a (C3-C9)-heterocycloalkenyl, wherein the cycloalkyl, heterocycloalkyl and heterocycloalkenyl are unsubstituted or mono, di- or tri-substituted by halogen, CF3, (C1-C6) alkyl or (C0-C4) alkylene-O-(C0-C4) alkylene-H;

m is 0,1 or 2;

or a stereoisomer or enantiomer or a mixture in any ratio thereof, or a physiologically acceptable salt thereof, or a tautomer thereof.

2. The compound according to claim 1, wherein
R1 is (C1-C6) alkyl, (C0-C6) alkylene(C3-C6) cycloalkyl, (C0-C6) alkylene-(C6-C14)aryl, or (C0-C6) alkylene-(C5-C15) heteroaryl, wherein the alkyl, alkylene, aryl, heteroaryl and cycloalkyl are unsubstituted or mono-, di- or tri-substituted by F, Cl, Br, (C1-C6) alkyl, O-(C1-C6) alkyl, CF$_3$, OCF$_3$, or CN;

R2 and R3 are independently H, halogen, (C1-C6) alkyl, (C0-C4) alkylene-O-(C0-C4) alkylene-H, CN, or COO (C1-C6) alkyl, wherein the alkyl and alkylene are unsubstituted or mono-, di- or tri-substituted by F; and R4, R5, R6 and R7 are independently H, (C1-C6) alkyl, (C0-C6) alkylene-(C3-C6) cycloalkyl, or (C0-C6) alkylene-(C6-C14)aryl, wherein the alkyl, alkylene and cycloalkyl are unsubstituted or mono, di- or tri-substituted by halogen, (C1-C6) alkyl, (C0-C6) alkylene-O-(C0-C6)-alkylene-H, or CF$_3$, and wherein the alkyl and cycloalkyl are unsubstituted or mono-, di- or trisubstituted by halogen, CF3, (C1-C6) alkyl and (C0-C4) alkylene-O-(C0-C4) alkylene-H, and wherein at least one pair of R4 and R5, R6 and R7, R5 and R6, together with the C-atomes to which they are connected, or R6 together with the ortho C-Atom of the aromatic ring, form a (C3-C9) cycloalkyl, or a (C3-C9)-heterocycloalkyl wherein the cycloalkyl and heterocycloalkyl are unsubstituted or mono-, di- or tri-substituted by halogen, CF3, (C1-C6) alkyl or (C0-C4) alkylene-O-(C0-C4) alkylene-H;

or a stereoisomer or enantiomer or a mixture in any ratio thereof, or a physiologically acceptable salt thereof, or a tautomer thereof.

3. The compound according to claim 1, wherein
R1 is (C1-C6) alkyl, (C0-C6) alkylene-(C3-C6) cycloalkyl, or (C0-C6) alkylene-(C6-C14)aryl, wherein the alkyl, alkylene, aryl, and cycloalkyl are unsubstituted or mono-, di- or tri-substituted by F;

or a stereoisomer or enantiomer or a mixture in any ratio thereof, or a physiologically acceptable salt thereof, or a tautomer thereof.

4. The compound according to claim 1, wherein
R2 and R3 are independently H, halogen, (C1-C6) alkyl, or (C0-C4) alkylene-O-(C0-C4) alkylene-H, wherein the alkyl and alkylene are unsubstituted or mono-, di- or tri-substituted by F;

or a stereoisomer or enantiomer or a mixture in any ratio thereof, or a physiologically acceptable salt thereof, or a tautomer thereof.

5. The compound according to claim 1, wherein
R4, R5, R6 and R7 are independently H or (C1-C6) alkyl;
and wherein at least one pair of R4 and R5 or R5 and R6 together with the C-atoms to which they are connected, or R6 together with the ortho C-atom of the aromatic ring, form a (C3-C9) cycloalkyl, wherein the cycloalkyl is unsubstituted or mono-substituted by (C1-C6) alkyl;

or a stereoisomer or enantiomer or a mixture in any ratio thereof, or a physiologically acceptable salt thereof, or a tautomer thereof.

6. The compound according to claim 1, wherein
R1 is (C1-C6) alkyl, (C3-C6) cycloalkyl or phenyl, wherein the alkyl is unsubstituted or mono-, di- or trisubstituted by F;

R2 and R3 are independently H, halogen, (C1-C6) alkyl, or O-(C1-C4) alkylene-H, wherein the alkyl and alkylene are unsubstituted or mono-, di- or tri-substituted by F;

R4, R5, R6 and R7 are independently H, or (C1-C6) alkyl, wherein the alkyl is unsubstituted or mono-, di- or tri-substituted by halogen or (C1-C6) alkyl;

and wherein at least one pair of R4 and R5, R6 and R7, R5 and R6, together with the C-atoms to which they are connected, or R6 together with the ortho C-atom of the aromatic ring, form a (C3-C7) cycloalkyl, wherein the cycloalkyl is unsubstituted or mono-, di- or tri-substituted by (C1-C6) alkyl;

or a stereoisomer or enantiomer or a mixture in any ratio thereof, or a physiologically acceptable salt thereof, or a tautomer thereof.

7. The compound according to claim 1, wherein
R1 is (C1-C6) alkyl, which is unsubstituted or mono-, di- or tri-substituted by F;
R2 and R3 are H;
R4 and R7 are H; and
the pair of R5 and R6 together with the C-atoms to which they are connected form a (C3-C7) cycloalkyl;
or a stereoisomer or enantiomer or a mixture in any ratio thereof, or a physiologically acceptable salt thereof, or a tautomer thereof.

8. The compound according to claim 1, wherein
R1 is (C1-C6) alkyl, which is unsubstituted or mono-, di- or tri-substituted by F;
R2 and R3 are H;
R6 and R7 are H;
the pair of R4 and R5 together with the C-atomes to which they are connected form a (C3-C7) cycloalkyl;
or a stereoisomer or enantiomer or a mixture in any ratio thereof, or a physiologically acceptable salt thereof, or a tautomer thereof.

9. The compound according to claim 1, wherein
R1 is (C1-C6) alkyl, (C3-C6) cycloalkyl or phenyl, wherein the alkyl is unsubstituted or mono-, di- or trisubstituted by F;
R2 is H, Cl, (C1-C4) alkyl, or O-(C1-C4) alkylene-H, wherein the alkyl and alkylene are unsubstituted or mono-, di- or tri-substituted by F;
R3, R5, R7 are H;
R4 is H or (C1-C4) alkyl; and
R6 together with the ortho C-atom of the aromatic ring form a (C3-C7) cycloalkyl, wherein the cycloalkyl is unsubstituted or substituted by (C1-C4) alkyl;
or a stereoisomer or enantiomer or a mixture in any ratio thereof, or a physiologically acceptable salt thereof, or a tautomer thereof.

10. A pharmaceutical composition comprising the compound according to claim 1 or a stereoisomer or enantiomer or a mixture in any ratio thereof, or a physiologically acceptable salt thereof, or a tautomer thereof, in combination with a pharmaceutically suitable carrier.

11. The pharmaceutical composition according to claim 10, further comprising one active substance which has an favorable effect on metabolic disturbance or a disorder frequently associated therewith.

12. The pharmaceutical composition according to claim 11, wherein the active substance is an antidiabetic agent.

13. The pharmaceutical composition according to claim 11, wherein the active substance is a lipid modulator.

14. A process for preparing the pharmaceutical composition comprising the compound according to claim 1 or a stereoisomer or enantiomer or a mixture in any ratio thereof, or a physiologically acceptable salt thereof, or a tautomer thereof, in combination with a pharmaceutically suitable carrier, comprising mixing the compound according to claim 1 or the stereoisomer or enantiomer or the mixture in any ratio thereof, or the physiologically acceptable salt thereof, or the tautomer thereof with the pharmaceutically suitable carrier, and bringing this mixture into a form suitable for administration.

* * * * *

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial
<220> FEATURE:
<223> OTHER INFORMATION: GLP-1 Derivative

<400> SEQUENCE: 1

Phe Ile Ala Trp Leu Val Lys Glu Lys Ala Ala Gln Gly Glu Ser Asp
1               5                   10                  15

Val Ser Ser Tyr Leu Thr Phe Thr Gly Glu
            20                  25

<210> SEQ ID NO 2
<211> LENGTH: 19
<212> TYPE: DNA
<213> ORGANISM: Artificial
<220> FEATURE:
<223> OTHER INFORMATION: primer

<400> SEQUENCE: 2
ctcggaggac agtactccg                                              19
```